(12) United States Patent
Carlini et al.

(10) Patent No.: US 8,460,447 B2
(45) Date of Patent: *Jun. 11, 2013

(54) SUBSTITUTED OXAZOLINE COMPOUNDS OR SUBSTITUTED OXAZOLINE DERIVATIVES

(75) Inventors: Rina Carlini, Oakville (CA); Guerino G. Sacripante, Oakville (CA); Stephan V. Drappel, Toronto (CA); Bo Wu, Wilsonville, OR (US)

(73) Assignee: Xerox Corporation, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/095,221

(22) Filed: Apr. 27, 2011

(65) Prior Publication Data

US 2012/0272859 A1    Nov. 1, 2012

(51) Int. Cl.
*C09D 11/00*    (2006.01)
*C07D 263/08*    (2006.01)

(52) U.S. Cl.
USPC ........................................ 106/31.13; 548/237

(58) Field of Classification Search
None
See application file for complete search history.

(56) References Cited

U.S. PATENT DOCUMENTS

| | | | |
|---|---|---|---|
| 3,235,557 A | 2/1966 | Frederick et al. |
| 3,308,024 A | 3/1967 | Frederick et al. |
| 4,153,566 A | 5/1979 | Ryer et al. |
| 4,169,836 A | 10/1979 | Ryer et al. |
| 5,195,430 A | 3/1993 | Rise |
| 5,231,135 A | 7/1993 | Machell et al. |
| 5,372,852 A | 12/1994 | Titterington et al. |
| 5,389,958 A | 2/1995 | Bui et al. |
| 5,496,879 A | 3/1996 | Griebel et al. |
| 5,621,022 A | 4/1997 | Jaeger et al. |
| 5,698,017 A | 12/1997 | Sacripante et al. |
| 5,817,169 A | 10/1998 | Sacripante et al. |
| 6,472,523 B1 | 10/2002 | Banning et al. |
| 6,547,380 B2 | 4/2003 | Smith et al. |
| 6,713,614 B2 | 3/2004 | Carlini et al. |
| 6,958,406 B2 | 10/2005 | Banning et al. |
| 6,998,493 B2 | 2/2006 | Banning et al. |
| 7,063,410 B2 | 6/2006 | Slotto et al. |
| 7,084,190 B2 | 8/2006 | Everhardus et al. |
| 7,211,131 B2 | 5/2007 | Banning et al. |
| 7,294,730 B2 | 11/2007 | Banning et al. |
| 7,448,719 B1 | 11/2008 | Newell |
| 2009/0297714 A1 | 12/2009 | Wong et al. |
| 2010/0086683 A1 | 4/2010 | Birau et al. |
| 2010/0313788 A1 | 12/2010 | Drappel et al. |

FOREIGN PATENT DOCUMENTS

PL             196811      * 2/2008

OTHER PUBLICATIONS

PL 196811 SciFinder Abstract.*
Garrett C. Moraski et al., "Structure-activity relationship of new anti-tuberculosis agents derived from oxazoline and oxazole benzyl esters" European Journal of Medicinal Chemistry 45, (2010), 1703-1716.
Robert C. Elderfield, "Five-membered Heterocycles Containing Two Hetero Atoms and their Benzo Derivatives", Heterocyclic Compound, 1957, Chapter 5, pp. 298-417, vol. 5, John Wiley and Sons, Inc., New York.
U.S. Appl. No. 13/095,795, filed Apr. 27, 2011 Kentaro Morimitsu et al.
U.S. Appl. No. 13/095,555, filed Apr. 27, 2011 Naveen Chopra et al.
U.S. Appl. No. 13/095,591, filed Apr. 27, 2011 Jennifer Belelie et al.
U.S. Appl. No. 13/095,784, filed Apr. 27, 2011 Kentaro Morimitsu et al.
U.S. Appl. No. 13/095,715, filed Apr. 27, 2011 Kentaro Morimitsu et al.
U.S. Appl. No. 13/095,770, filed Apr. 27, 2011 Kentaro Morimitsu et al.
U.S. Appl. No. 13/095,681, filed Apr. 27, 2011 Jennifer Belelie et al.
U.S. Appl. No. 13/095,636, filed Apr. 27, 2011 Jennifer Belelie et al.
U.S. Appl. No. 13/095,174, filed Apr. 27, 2011 Rina Carlini et al.
U.S. Appl. No. 13/095,015, filed Apr. 27, 2011 Thomas Edward Enright et al.
U.S. Appl. No. 13/095,028, filed Apr. 27, 2011 Kentaro Morimitsu et al.
U.S. Appl. No. 13/095,043, filed Apr. 27, 2011 Peter G. Odell et al.
U.S. Appl. No. 13/095,038, filed Apr. 27, 2011 Paul Mcconville et al.

* cited by examiner

*Primary Examiner* — Yun Qian
(74) *Attorney, Agent, or Firm* — Oliff & Berridge, PLC

(57)    ABSTRACT

Substituted oxazoline compounds and/or substituted oxazoline derivatives having amorphous, semi-crystalline, or crystalline properties and methods for producing such compounds and derivatives are presented. The substituted oxazoline compounds and/or substituted oxazoline derivatives are useful for various applications. For example, the substituted oxazoline compounds and/or substituted oxazoline derivatives may function as phase-change agents, a binder resins, rheology modifiers or plasticizers for ink compositions.

20 Claims, 3 Drawing Sheets

SUBSTITUTED OXAZOLINE COMPOUNDS OR SUBSTITUTED OXAZOLINE DERIVATIVES

CROSS-REFERENCE TO RELATED APPLICATIONS

Commonly assigned U.S. patent application Ser. No. 13/095,174, entitled "Ink Compositions Incorporating Substituted Oxazoline Compounds or Substituted Oxazoline Derivatives,") to Rina Carlini et al.; commonly assigned U.S. patent application Ser. No. 13/095,784, entitled "Solid Ink Compositions Comprising Amorphous Esters of Tartaric Acid") to Kentaro Morimitsu et al.; commonly assigned patent application Ser. No. 13/095,715, entitled "Solid Ink Compositions Comprising Crystalline Esters of Tartaric Acid"), to Kentaro Morimitsu et al.; commonly assigned U.S. patent application Ser. No. 13/095,770, entitled "Phase Change Inks and Methods of Making the Same") to Kentaro Morimitsu et al.; commonly assigned U.S. patent application Ser. No. 13/095,591, entitled "Phase Change Ink Components and Methods of Making the Same") to Jennifer Belelie et al.; commonly assigned U.S. patent application Ser. No. 13/095,555 entitled, "Phase Change Inks and Methods of Making the Same") to Naveen Chopra et al.; commonly assigned U.S. patent application Ser. No. 13/095,681 entitled, Solid Ink Compositions Comprising Crystalline-Amorphous Mixtures") to Jennifer Belelie et al.; commonly assigned U.S. patent application Ser. No. 13/095,795, entitled "Solid Ink Compositions Comprising Amorphous Esters of Citric Acid") to Kentaro Morimitsu et al.; commonly assigned U.S. patent application Ser. No. 13/095,636, entitled "Solid Ink Compositions Comprising Crystalline-Amorphous Mixtures") to Jennifer Belelie et al.; commonly assigned U.S. patent application Ser. No. 13/095,038, entitled "Print Process For Phase Separation Ink"), Paul McConville et al.; commonly assigned U.S. patent application Ser. No. 13/095,015, entitled "Solventless Reaction Process"), Thomas Edward Enright et al.; commonly assigned U.S. patent application Ser. No. 13/095,028, entitled "Phase Change Ink"), Kentaro Morimitsu, et al.; and commonly assigned U.S. patent application Ser. No. 13/095,043, entitled "Phase Separation Ink"), Peter G. Odell, et al. concurrently filed herewith, the disclosures of which are totally incorporated herein by reference in there entireties.

TECHNICAL FIELD

This disclosure is generally directed to compositions comprising substituted oxazoline compounds and/or substituted oxazoline derivatives. Such compositions may be incorporated into a various other substances, such as ink compositions. For example, the substituted oxazoline compounds and/or substituted oxazoline derivatives may function as phase-change agents, binder resins, compatibilizing agents, synergists, rheology modifiers or plasticizers of phase change ink compositions.

BACKGROUND

Phase change inks (sometimes referred to as "solid inks" and "hot melt inks") have been used in various liquid deposition techniques. Phase change inks often contain a "phase-change agent" that enables the ink to exist in a solid phase at ambient temperatures, but also exist in the liquid phase at the elevated operating temperature of an ink jet printing device. At the printhead operating temperature, droplets of liquid ink are ejected from the printing device and, as the ink is jetted towards or contacts the surface of the recording substrate, either directly or via an intermediate heated transfer belt or drum, the ink solidifies onto the substrate to form a predetermined pattern of solid ink marks. Phase change inks have also been used in other printing technologies, such as gravure printing, as disclosed in, for example, U.S. Pat. No. 5,496,879, the entire disclosure of which is totally incorporated herein by reference. Phase change inks have also been used for applications such as postal marking, industrial marking, labeling, and for rapid 3-dimensional prototyping of objects.

Phase change inks are desirable for ink jet printers because they remain in a solid phase at room temperature, which is convenient during shipping and ink handling, enables long term storage, and ease of use. In addition, the problems associated with nozzle clogging as a result of ink evaporation with other aqueous or solvent-based liquid ink jet inks are largely eliminated, thereby greatly improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and image quality is improved.

Ink jet printing systems generally are of two types: continuous stream and drop-on-demand, as described in U.S. Pat. No. 6,547,380. The entire disclosures of U.S. Pat. Nos. 5,195,430 and 6,547,380 are totally incorporated herein by reference.

There are at least three types of drop-on-demand ink jet systems. One type of drop-on-demand system is a piezoelectric device that has as its major components an ink filled channel or passageway having a nozzle on one end and a piezoelectric transducer near the other end to produce pressure pulses. Another type of drop-on-demand system is known as acoustic ink printing. Still another type of drop-on-demand system is known as thermal ink jet, or bubble jet, and produces high velocity droplets.

In general, phase change inks are in the solid phase at, for example, ambient or room temperature, such as about 20° C. to about 25° C., but exist in the liquid phase at the elevated operating temperature of an ink jet printing device. At the jet operating temperature, the ink is molten and droplets of liquid ink are ejected from the printing device.

In a typical design of a piezoelectric ink jet device utilizing phase change inks, whether printed directly onto a substrate or onto an intermediate transfer member, such as the ones described in U.S. Pat. Nos. 5,372,852; 7,063,410; and 7,448,719 the disclosures of which are hereby incorporated by reference in their entireties, droplets of liquid ink are ejected from the printing device at the printhead operating temperature. When the ink droplets contact the surface of the recording substrate, either directly or via an intermediate heated transfer belt or drum, they rapidly solidify to form a predetermined pattern of solidified ink drops.

Many phase change inks typically used with ink jet printers are comprised of (semi)crystalline and polymer waxes as part of the ink vehicle (or ink base). Crystalline waxes and other functional wax components enable the sharp melting of the ink and narrow phase-change transitions from the molten liquid state to the solid state. The wax components also reduce the coefficient of friction of the printed image, which aids the automated feeding of printed documents across the glass platen and other subsystems of the printer. Such wax-based, phase change ink jet inks provide vivid color images.

In typical systems, these crystalline wax inks partially cool on an intermediate transfer member and are then pressed into the image receiving medium such as paper. Transfuse action spreads the image droplet, providing a richer color and lower pile height. The low flow of the solid ink also prevents show through on the paper.

However, the use of crystalline waxes can pose some limitations on the printed image. Conventional crystalline waxes are non-polar hydrocarbon polymers and aliphatic molecules, which are attracted together by weak, non-covalent van der Waals forces. Such waxes typically have poor adhesion to paper substrates because there is low affinity for the higher polarity paper. This mismatch of intermolecular forces and polarity between ink and substrate can make the wax-based phase change prints vulnerable to mechanical damage, such as abrasions and creases. There is consequently a need for new phase change ink compositions having higher polarity than wax-based inks and that have good affinity for a wide variety of paper substrates. There is also a need for new phase change ink compositions of higher polarity and good compatibility with commercially available colorants and ink additives. There is furthermore a need for such new ink compositions to have improved durability on paper substrates compared with wax-based phase change inks.

Oxazolines are a promising class of heterocyclic compounds, which have been previously reported for medical, pharmaceutical and veterinary uses, and also as additives in personal care and consumer product formulations, such as shampoos, detergents and the like, and in oleaginous compositions such as mechanical lubricating oils and as oil and sludge dispersants. Oxazolines may be prepared efficiently in one or more reaction steps from simple starting materials, which are typically an organic carboxylic acid and a primary amino alcohol. Detailed reviews of the chemistry of oxazoles and oxazoline compounds are known, as illustrated by R. H Wiley and L. L. Bennett in *Chemical Reviews*, volume 44, pages 447 to 476 (1949), and also extensively described by J. W. Cornforth in *Heterocyclic Compound*, 1957, chapter 5, pages 300-417, the disclosures of which are totally incorporated herein by reference in their entireties. Furthermore, oxazoline derivatives being the major product from the reaction of an organic acid and amino alcohol is also known, such as disclosed by A. I. Meyers and D. L. Temple in the *Journal of the Chemical Society*, volume 92, page 6644 (1970), the disclosure of which is totally incorporated herein by reference.

In European Journal of Medicinal Chemistry 45, (2010), 1703-1716, Garrett C. Moraski et al. describes low toxicity anti-tuberculosis agents derived from o-hydroxy phenyl-oxazoline and o-hydroxy phenyl-oxazole benzyl esters (illustrated below).

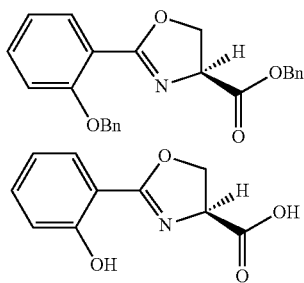

In U.S. Pat. Nos. 3,235,557 and 3,308,024, L. S. Wiggins and coworkers (assigned to Aspro-Nicholas Ltd.) describe 5,5-bis(hydroxymethyl) substituted halo-, trifluoromethyl, or o-hydroxy-phenyloxazoline compounds and their salts which provide tranquilization and anti-convulsant for animals. (illustrated below).

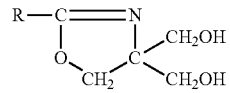

In U.S. Pat. No. 4,169,836, J. Ryer et al. (Exxon Research and Engineering Co.) discloses mono-oxazoline and bis-oxazoline compounds as in Formula (A) prepared from alkenyl succinic anhydrides having at least 8 carbons in said alkenyl group, which is reacted with 1 to maximum of 2 mole equivalents of a 2,2-disubstituted-2-amino-1-alkanols, wherein the latter has 2 to 3 hydroxy groups and containing 4 to 8 carbons represented by the formula (B), wherein X is an hydroxyallyl group such as —$(CH_2)_n$OH with n being from 1 to 3. The oxazoline compounds are disclosed to have use as additives for oil-containing compositions such as dispersants for oil sludges and oil lubricants, as well as anti-corrosion agents in gasoline. In a related disclosure, U.S. Pat. No. 4,153,566 to J. Ryer et al. (Exxon Research and Engineering Co.) describes lubricating oil compositions comprising oxazoline reaction products derived from C4-C10 mono-unsaturated dicarboxylic acid derivatives.

Monomeric oxazolines have been developed as the phase-change ink components for the Acoustic Ink Printing (AIP) technology of 1990's, as in U.S. Pat. Nos. 5,817,169 and 5,698,017. The entire disclosures of U.S. Pat. Nos. 5,817,169 and 5,698,017 are totally incorporated herein by reference. For example, U.S. Pat. No. 5,698,017 to Sacripante et al. discloses an ink composition consisting of a colorant, a vehicle component and optionally an amide or an amino ester, and which vehicle consists essentially of the condensation product of an organic acid and an amino alcohol, and which product consists essentially of an oxazoline or benzoxazoline wherein the oxazoline or benzoxazoline are represented by the following general formulas:

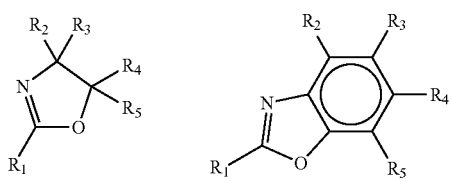

wherein $R_1$ is an alkyl group of from about 1 to about 55 carbon atoms, $R_2$, $R_3$, $R_4$ and $R_5$ are alkyl, an alkyl alcohol or an alkyl ester, each alkyl containing from about 1 to about 55 carbon atoms; and U.S. Pat. No. 5,817,169 to Sacripante et al. discloses an ink composition comprised of a colorant and a vehicle component, and which vehicle component is comprised of the condensation product of an organic acid and an amino alcohol, and a mixture of an amide and an amino ester, and wherein said mixture contains from about 1 to about 99 parts of said amide and from about 99 parts to about 1 part of said ester.

While the known compositions and processes may be suitable for their intended purposes, a need remains for phase change ink compositions suitable for ink jet printing under a variety of conditions, such as direct-to-paper (DTP) printing conditions. In addition, there is a need for phase change ink compositions that are compatible with a wide variety of papers that generate high quality images on a wide variety of papers at low cost. These and other needs and advantages can be achievable with the compositions comprising substituted oxazoline compounds and/or substituted oxazoline derivatives of the present disclosure.

SUMMARY

This disclosure provides a composition including substituted oxazoline compounds and/or substituted oxazoline derivatives, the composition comprising:

one or more compounds represented by General Formula I $$\text{(I)}$$

wherein $R_1$ is an alkylene group, arylene group, arylalkylene group, alkylarylene group; and $R_2$ is an alkyl group, aryl group, alkylaryl group, aromatic group (each of which may or may not be substituted), a hydrogen, —(C=O)—(CH$_2$)$_n$CH$_3$ in which n is zero or an integer in a range from 1 to about 50, or wherein $R_y$ is H, OH, OCH$_3$, Cl, Br, F, I, NH(COCH$_3$), CH$_3$, CH$_2$CH$_3$, isopropyl, t-butyl, CO$_2$CH$_3$, CO$_2$H, an alkyl group having from 1 to about 66 carbons or from about 2 to about 18 carbons, or alkoxy group having from 1 to about 8 carbons or from about 2 to about 6 carbons, or —(C=O)—NH—$R_2$, where $R_z$ is either a linear alkyl group of the formula —(CH$_2$)$_n$CH$_3$ wherein n is either zero or an integer of from 1 to about 36, such as an integer of from 2 to about 24, or an integer of from about 5 to about 20, or where $R_2$ is an alkylaryl group containing from about 6 to about 20 carbon atoms, such as from about 7 to about 18 carbon atoms, or from about 7 to about 14 carbon atoms (where each $R_2$ group may be the same or different so as to give either symmetrical or unsymmetrical structures);

one or more compounds represented by General Formula II $$\text{(II)}$$

wherein $R_4$ is an alkyl group, aryl group, alkylaryl group, or an aromatic group, each of which may or may not be substituted (where each $R_4$ group may be the same or different so as to give either symmetrical or unsymmetrical structures depending on the identity of each $R_5$ group (i.e., whether each $R_5$ group is the same or different));

$R_5$ is an alkyl group, aryl group, alkylaryl group, aromatic group (each of which may or may not be substituted), a hydrogen, —(C=O)—(CH$_2$)$_n$CH$_3$ in which n is zero or an integer in a range from 1 to about 50, or wherein $R_y$ is H, OH, OCH$_3$, Cl, Br, F, I, NH(COCH$_3$), CH$_3$, CH$_2$CH$_3$, isopropyl, t-butyl, CO$_2$CH$_3$, CO$_2$H, an alkyl group having from 1 to about 66 carbons or from about 2 to about 18 carbons, or alkoxy group having from 1 to about 8 carbons or from about 2 to about 6 carbons, aryl group or alkylaryl group, or —(C=O)—NH—$R_z$, where $R_z$ is either a linear alkyl group of the formula —(CH$_2$)$_n$CH$_3$ wherein n is either zero or an integer of from 1 to about 36, such as an integer of from 2 to about 24, or an integer of from about 5 to about 20, or where $R_z$ is an alkylaryl group containing from about 6 to about 20 carbon atoms, such as from about 7 to about 18 carbon atoms, or from about 7 to about 14 carbon atoms (where each $R_5$ group may be the same or different so as to give either symmetrical or unsymmetrical structures depending on the identity of each $R_4$ group (i.e., whether each $R_4$ group is the same or different));

$R_6$ is an alkylene group, arylene group, arylalkylene group, alkylarylene group, in which n is an integer in a range from about 6 to about 36, one or more compounds represented by General Formula III $$\text{(III)}$$

in which m is an integer of from 1 to about 100, wherein $R_7$ is an alkyl group, aryl group, alkylaryl group, aromatic group (each of which may or may not be substituted), or a hydrogen; and $R_8$ is an alkylene group, arylene group, arylalkylene group, alkylarylene group,

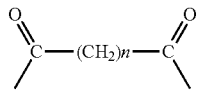

in which n is an integer in a range from about 6 to about 36,

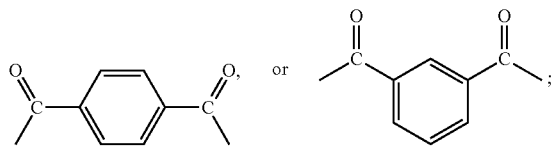

or one or more compounds represented by General Formula IV

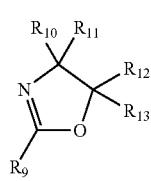

wherein $R_9$ is an alkyl group, aryl group, alkylaryl group, or aromatic group (each of which may or may not be substituted), such as an alkyl group, aryl group, alkylaryl group, or aromatic group, a linear, cyclic or branched saturated alkyl group, or aromatic group, such as, for example,

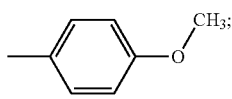

$R_{10}$, $R_{11}$, $R_{12}$ and $R_{13}$ are the same or different and are an alkyl group, aryl group, alkylaryl group, alkoxy group, hydroxyalkyl group, or aromatic group (each of which may or may not be substituted), such as a linear, cyclic or branched alkyl, a linear, cyclic or branched alkyl alcohol, a linear, cyclic or branched alkyl ester, or an aryl ester, wherein at least one of $R_9$, $R_{10}$, $R_{11}$, $R_{12}$ and $R_{13}$ is an aromatic group, which may or may not be a substituted aromatic group.

This disclosure also provides a method for producing substituted oxazoline compounds and/or substituted oxazoline derivatives represented by the above general formulas.

DESCRIPTION OF THE EMBODIMENTS

Figure 1:
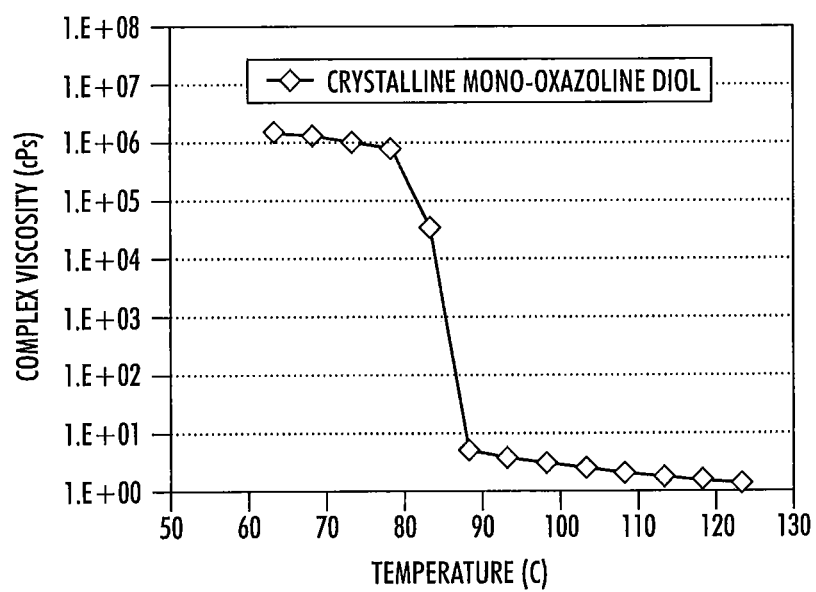
FIG. 1 is an illustration of the rheological profile of a crystalline mono-oxazoline (Example 3).

Described herein are compositions that comprise substituted oxazoline compounds and/or substituted oxazoline derivatives. In embodiments, such compositions may be incorporated, for example, as components for ink compositions or coatings such as phase-change agents, binder resins, compatibilizing agents, synergists, rheology modifiers or plasticizers. Oxazoline compounds or derivatives have also been used for medical, pharmaceutical and veterinary uses, as additives in personal care and consumer product formulations, and in oleaginous compositions such as, for example, lubricant oils and as oil dispersants. In embodiments, the compositions may be composed of one or more substituted oxazoline compound or substituted oxazoline derivatives.

The substituted oxazoline compounds and/or substituted oxazoline derivatives of this disclosure include various mono-oxazolines, dimer-oxazolines (or, bis-oxazolines) and poly-oxazolines that are tethered with a spacer group in one of two ways: a) connected at C2 of the oxazoline ring, or b) connected by functional group substituents (for example, ester, urethane, amide, and the like) at C5 of the oxazoline ring, and poly-oxazolines. Depending on the identity of the substituent groups on the substituted oxazoline compounds and/or substituted oxazoline derivatives, the compounds of the present disclosure have the ability to demonstrate a variety of physical properties, such as crystalline, semi-crystalline or amorphous properties. For example, the onset of crystallization temperature (and onset of melting temperature) of certain oxazoline compounds can be tuned by changing the type of the substituent group on the oxazoline ring, such as for example the alkyl group chain length. The rheological properties of substituted oxazoline compounds and/or substituted oxazoline derivatives maybe tuned accordingly, such as by converting them into esters. This ability to tune the rheological characteristics of some of the substituted oxazoline compounds and/or substituted oxazoline derivatives of this disclosure by the suitable choice of the functional group on the oxazoline ring, such as an ester group, enables the design of oxazoline-based materials having either crystalline, amorphous or even semi-crystalline properties, which is advantageous for use in certain applications, such as for inkjet printing of phase change ink compositions.

In this specification and the claims that follow, singular forms such as "a," "an," and "the" include plural forms unless the content clearly dictates otherwise. In addition, reference may be made to a number of terms that shall be defined as follows:

The term "major component" refers, for example, to a mixture or composition that includes multiple ingredients or components and specifies the particular ingredient or component that makes up the largest proportion of the mixture or composition.

The terms "one or more" and "at least one" refer, for example, to instances in which one of the subsequently described circumstances occurs, and to instances in which more than one of the subsequently described circumstances occurs.

The term "saturated" refers, for example, to compounds containing only single bonds, and in this specification, also includes cyclic structures. The term "unsaturated" refers, for example, to compounds that contain one or more double bonds and/or one or more triple bonds, which may include carbon atoms and/or heteroatoms such as O, N, S, and P.

The terms "hydrocarbon" and "alkane" refer, for example, to branched and unbranched molecules having the general formula $C_nH_{2n+2}$, in which n is an integer having a value of 1 or more, such as of from 1 to about 60. Exemplary alkanes include methane, ethane, n-propane, isopropane, n-butane, isobutane, tert-butane, octane, decane, tetradecane, hexadecane, eicosane, tetracosane, isomeric forms thereof, and the like. Alkanes may be substituted by replacing hydrogen atoms with one or more functional groups. The term "aliphatic" refers, for example, to hydrocarbon molecules that are acyclic, linear or branched alkanes. The term "long-chain" refers, for example, to linear hydrocarbon chains in which n is a number of from about 8 to about 60, such as from about 18 to about 45 or from about 24 to about 40. The term "short-chain" refers, for example, to linear hydrocarbon chains in which n is a number of from 1 to about 7, such as from about 2 to about 5 or from about 3 to about 4. The term "cyclic" or "cycloaliphatic" refers, for example, to cyclic hydrocarbon molecules that comprised one or more rings, and wherein the rings can be fused, branched or polycyclic, such as a bicyclic ring.

The term "alkyl" refers, for example, to a saturated hydrocarbon group that is acyclic or cyclic, and either branched or unbranched, derived from an alkane and having the general formula $C_nH_{2n+1}$ or $C_nH_{2n-1}$, in which n is an integer having a value of 1 or more. For example, n may be in the range from 1 to about 60. Exemplary alkyl groups include methyl, ethyl, n-propyl, isopropyl, n-butyl, isobutyl, sec-butyl, tert-butyl, n-pentyl, neo-pentyl, cyclopentyl, n-hexyl, cyclohexyl, n-octyl, iso-octyl, cyclooctyl, decyl, tetradecyl, hexadecyl, eicosyl, tetracosyl, isomeric forms thereof, and the like. The term "lower alkyl" refers, for example, to an alkyl group of from 1 to about 12 carbon atoms.

The term "alkene" refers, for example, to branched and unbranched unsaturated molecules that are derived from alkenes and include one or more double bonds between carbon atoms. Exemplary alkenes include ethylene, propene, butene, butadiene, octene, decene, tetradecene, hexadecene, eicosene, tetracosene and the like. Alkenes may be substituted by replacing hydrogen atoms with one or more functional groups.

The term "alkenyl" refers, for example, to a branched or unbranched unsaturated hydrocarbon group containing one or more double bond and derived from an alkene. Exemplary alkenyl groups include ethylenyl, propenyl, butenyl, octenyl, decenyl, tetradecenyl, hexadecenyl, eicosenyl, tetracosenyl and the like. The term "lower alkenyl" refers, for example, to an alkenyl group of from 1 to about 12 carbon atoms.

The term "alkyne" refers, for example, to branched and unbranched unsaturated molecules that are derived from alkanes and include one or more triple bonds between carbon atoms. Exemplary alkynes include ethyne, propyne, butyne, octyne, decyne, tetradecyne, hexadecyne, eicosyne, tetracosyne and the like. Alkynes may be substituted by replacing hydrogen atoms with one or more functional groups.

The term "alkynyl" refers, for example, to a branched or unbranched unsaturated hydrocarbon group containing one or more triple bonds and derived from an alkyne. Exemplary alkynyl groups include ethynyl, propynyl, butynyl, octynyl, decynyl, tetradecynyl, hexadecynyl, eicosynyl, tetracosynyl and the like.

The term "aromatic" refers to aromatic compounds which have a functional group that contains a total of (4n+2) π electrons (where integer n is from 1 to 6) that are arranged in a conjugated and continuously delocalized manner within that group, and which may include heteroatoms such as O, N, S, B, Se, or Fe, and which may include one or more cyclic or ring systems that may include one or more fused aromatic or cycloaliphatic rings. Examples of aromatic compounds include, for example, benzene ($C_6H_6$), naphthalene ($C_{10}H_8$), anthracene ($C_{14}H_{10}$), phenanthrene ($C_{14}H_{10}$), pyridine ($C_5H_5N$), pyrrole ($C_4H_5N$), furan ($C_4H_4O$), thiophene ($C_4H_4S$), and the like. Optionally, these aromatic compounds may be substituted with one or more independently selected substituents, including alkyl and cycloalkyl, alkenyl, alkoxy, aryl, hydroxyl, thiol, halo (such as F, Cl, Br, I), (thio)ester, carboxylic acid, acyl, (alkyl)amino, (aryl)amino, and nitro groups.

The term "aryl" refers, for example, to an organic group derived from an aromatic compound and having the same general structure as the aromatic compound. Examples of aromatic compounds include, for example, phenyl($C_6H_5$), benzyl($C_7H_7$), naphthyl($C_{10}H_7$), anthracenyl($C_{14}H_9$), furanyl($C_4H_3O$), pyridinyl($C_5H_4N$), thiopheneyl($C_4H_3S$), and the like. Optionally, these aromatic groups may be substituted with one or more independently selected substituents, including alkyl and cycloalkyl, alkenyl, alkoxy, aryl, hydroxyl, thiol, halo (such as F, Cl, Br, I), (thio)ester, carboxylic acid, acyl, (alkyl)amino, (aryl)amino, and nitro groups.

The term "arylamine" refers, for example, to moieties containing both aryl and amine groups.

The term "alkoxy" refers, for example, to an alkyl group bound through a single, terminal ether linkage; that is, an "alkoxy" group is defined as —OR in which R is an alkyl as defined above. A "lower alkoxy" refers, for example, to an alkoxy group containing 1 to about 6 carbon atoms.

"Alcohol" refers, for example, to an alkyl moiety in which one or more of the hydrogen atoms has been replaced by an —OH group. The term "lower alcohol" refers, for example, to an alkyl group of about 1 to about 6 carbon atoms in which one or more of the hydrogen atoms has been replaced by an —OH group. The term "primary alcohol" refers, for example to alcohols in which the —OH group is bonded to a terminal carbon atom, such as in methanol, ethanol, 1-propanol, 1-butanol, 1-hexanol and the like. The term "secondary alcohol" refers, for example to alcohols in which the —OH group is bonded to a carbon atom that is bonded to two other carbon atoms, such as in 2-propanol (isopropanol), 2-butanol, 2-hexanol and the like. The term "tertiary alcohol" refers, for example to alcohols in which the —OH group is bonded to a carbon atom that is bonded to three other carbon atoms, such as in methylpropanol (tert-butanol) and the like.

The terms "halogen" or "halogen atom" refer, for example, to Group 7 elements such as fluorine (F), chlorine (Cl), bromine (Br), and iodine (I). The term "halo" refers, for example, to substitution of a halogen atom for a hydrogen atom in an organic compound. "Haloalkyl" refers, for example, to an alkyl moiety in which one or more of the hydrogen atoms has been replaced by a halogen atom. The term "perhalogenated" refers, for example, to a compound in which all of the hydrogen atoms have been replaced by halogen atoms, while the phrase "partially halogenated" refers, for example, to a compound in which less than all of the hydrogen atoms have been replaced by halogen atoms.

The term "alkylaryl" refers, for example, to groups comprising and alkyl moiety and an aryl moiety, wherein the alkyl portion of the alkylaryl group can be linear or branched, saturated or unsaturated, and cyclic or acyclic, and wherein heteroatoms either may or may not be present in either the aryl or the alkyl portion of the alkylaryl group, with from, for example, about 6 to about 50 carbon atoms in the alkylaryl chain, such as from about 6 to about 40 or from about 7 to about 20 carbon atoms, wherein the substituents on the substituted alkyl, aryl, arylalkyl, and alkylaryl groups may be, for example, halogen atoms, ether groups, aldehyde groups, ketone groups, ester groups, amide groups, imide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring.

The term "alkylene" refers, for example, to a divalent aliphatic group or alkyl group, including linear and branched, saturated and unsaturated, cyclic and acyclic, and substituted and unsubstituted alkylene groups, and wherein heteroatoms, such as oxygen, nitrogen, sulfur, silicon, phosphorus, boron, Mg, Li, Al, Ge, Cu, Fe, Ni, Pd, Pt and the like either may or may not be present in the alkylene group. For example, an alkylene group may have the structure —$(CH_2)_p$—, in which p is an integer in a range of from 1 to about 60, such as from about 5 to about 25, or about 7 to about 15.

The term "arylene" refers, for example, to a divalent aromatic group or aryl group, including substituted and unsubstituted arylene groups, and wherein heteroatoms, such as O, N, S, P, Si, B, Al, Li, Mg, Cu, Fe and the like either may or may not be present in the arylene group. For example, an arylene group may have about 5 to about 20 carbon atoms in the arylene chain, such as from about 6 to about 14 or from about 6 to about 10 carbon atoms.

The term "arylalkylene" refers, for example, to a divalent arylalkyl group, including substituted and unsubstituted arylalkylene groups, wherein the alkyl portion of the arylalkylene group can be linear or branched, saturated or unsaturated, and cyclic or acyclic, and wherein heteroatoms, such as O, N, S, P, Si, B, Al, Li, Mg, Cu, Fe, and the like either may or may not be present in either the aryl or the alkyl portion of the arylalkylene group. For example, an arylalkylene group may have about 6 to about 32 carbon atoms in the arylalkylene chain, such as from about 7 to about 22 or from about 7 to about 20 carbon atoms.

The term "alkylarylene" refers, for example, to a divalent alkylaryl group, including substituted and unsubstituted alkylarylene groups, wherein the alkyl portion of the alkylarylene group can be linear or branched, saturated or unsaturated, and cyclic or acyclic, and wherein heteroatoms, such as O, N, S, P, Si, Ge, B, Al, Li, Mg, Cu, Fe, Pd, Pt and the like either may or may not be present in either the aryl or the alkyl portion of the alkylarylene group. For example, the alkylarylene may have about 6 to about 32 carbon atoms in the alkylarylene chain, such as from about 7 to about 22 or from about 7 to about 20 carbon atoms, wherein the substituents on the substituted alkylene, arylene, arylalkylene, and alkylarylene groups can be, for example, halogen atoms, ether groups, aldehyde groups, ketone groups, ester groups, amide groups, imide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, cyano groups, pyridine groups, pyridinium groups, guanidinium groups, amidine groups, imidazolium groups, carboxylate groups, carboxylic acid groups, urethane groups, urea groups, mixtures thereof, and the like, wherein two or more substituents can be joined together to form a ring.

The term "derivative" refers, for example, to compounds that are derived from another compound and maintain the same general structure as the compound from which they are derived. For example, saturated alcohols and saturated amines are derivatives of alkanes.

As used herein, the term "viscosity" refers to a complex viscosity, which is the typical measurement provided by a mechanical spectrometer that is capable of subjecting a sample to a steady shear strain or a small amplitude sinusoidal deformation.

Substituted Oxazoline Compounds and/or Substituted Oxazoline Derivatives Represented by a Compound of "General Formula I."

In embodiments, the one or more substituted oxazoline compounds and/or substituted oxazoline derivatives may be represented by a compound of General Formula I having the general structure:

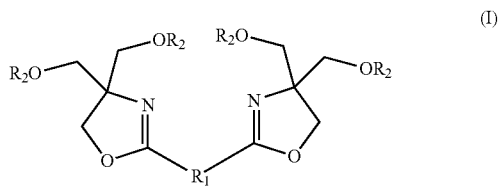

(I)

wherein $R_1$ is an alkylene group, arylene group, arylalkylene group, alkylarylene group, such an alkylene group containing from 1 to about 60 carbon atoms, or from about 2 to about 40 carbon atoms, or from about 4 to about 36 carbon atoms, or an arylene group, arylalkylene group, alkylarylene group containing from about 5 to about 20 carbon atoms, such as from about 6 to about 18 carbon atoms, or from about 7 to about 14 carbon atoms; and $R_2$ is an alkyl group, aryl group, alkylaryl group, aromatic group (each of which may or may not be substituted), or a hydrogen; for example, $R_2$ may be an alkyl group containing from 1 to about 60 carbon atoms, such as from 1 to about 30 carbon atoms, or from 1 to about 18 carbon atoms, or an aromatic group or aryl group containing from about 5 to about 20 carbon atoms, such as from about 6 to about 18 carbon atoms, or from about 7 to about 14 carbon atoms, or an acyl group of the general formula —(C=O)—$(CH_2)_n$$CH_3$, wherein n is either zero or an integer of from 1 to about 50, such as an integer of from about 4 to about 30, or an integer of from about 8 to about 16; or a urethane group of the general formula —(C=O)—NH—$R_z$, where $R_Z$ is either a linear alkyl group of the formula —$(CH_2)_n$$CH_3$ wherein n is either zero or an integer of from 1 to about 36, such as an integer of from 2 to about 24, or an integer of from about 5 to about 20, or where $R_z$ is an alkylaryl group containing from about 6 to about 20 carbon atoms, such as from about 7 to about 18 carbon atoms, or from about 7 to about 14 carbon atoms;

or group $R_2$ may be an alkylaryl, such as an alkylaryl group of the general formula

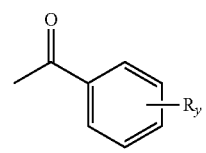

wherein $R_y$ is H, OH, $OCH_3$, Cl, Br, F, I, $NH(COCH_3)$, $CH_3$, $CH_2CH_3$, isopropyl, t-butyl, $CO_2CH_3$, $CO_2H$, an alkyl group having from 1 to about 66 carbons or from about 2 to about 18 carbons, or alkoxy group having from 1 to about 8 carbons or from about 2 to about 6 carbons.

In embodiments, the R group of the general formulas of the present disclosure, such as $R_2$ from the above formula, may be the same or different from each other. Unless designated otherwise, this concept applies to all formulas of the present disclosure (such as, for example, for $R_4$, $R_5$, $R_7$, $R_8$, $R_9$, $R_{10}$, $R_{11}$, $R_{12}$ and $R_{13}$, below). General Formula I may be used for an exemplary illustration of this concept. For example, with respect to General Formula I, each of the "$R_2$" groups may be the same or different from each other. In embodiments, one or more of the $R_2$ groups in General Formula I may be identical. Alternatively, in embodiments, each $R_2$ may be different from each other, as illustrated in the General Formula I below.

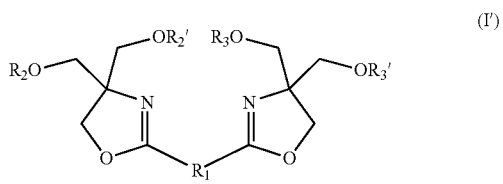

(I')

In another embodiment, $R_2$ and $R_2'$ are the same as each other, and optionally may be different or the same as either $R_3$ or $R_3'$. In another embodiment, $R_2$ and $R_2'$ are different from each other, and optionally may be different or the same as either $R_3$ or $R_3'$. In an embodiment, $R_3$ and $R_3'$ are the same as each other. In another embodiment, $R_3$ and $R_3'$ are different from each other.

In another embodiment, $R_3$ and $R_2'$ are the same as each other, and optionally may be different or the same as either $R_2$ or $R_3'$. In another embodiment, $R_3$ and $R_2'$ are different from each other, and optionally may be different or the same as either $R_2$ or $R_3'$.

In another embodiment, $R_2'$ and $R_3'$ are the same as each other, and optionally may be different or the same as either $R_2$ or $R_3$. In another embodiment, $R_3'$ and $R_2'$ are different from each other, and optionally may be different or the same as either $R_2$ or $R_3$.

In another embodiment, $R_2$ and $R_3$ are the same as each other, and are optionally different from $R_2'$ and $R_3'$. In another embodiment, $R_2$ and $R_3$ are different from each other, and are optionally different from $R_2'$ and $R_3'$.

In embodiments, $R_1$ may be of the general formula $C_{36}H_{64+n}$ and is a branched alkylene group which may include unsaturated groups and/or cyclic groups, wherein n is an integer of 0, 1, 2, 3, 4, 5, 6, 7, 8, 9, or 10, including, for example, structural isomers of the general formula

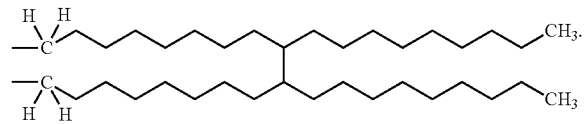

The compounds of General Formula I, where $R_2$ is a substituent other than hydrogen, may be prepared in two steps. The first step involves the synthesis of a dimer-oxazoline tetra-alcohol, where $R_2$ in the General Formula I is an H. In embodiments, the dimer-oxazoline tetra-alcohol may be prepared by a condensation reaction occurring at a suitable temperature, such as a high temperature condensation at a temperature above about 120° C., or in the range of from about 120° C. to about 220° C., or in the range of from about 150° C. to about 210° C., of a suitable diacid having an $R_1$ group as defined above with at least 2 molar equivalents of tris(hydroxymethyl)aminomethane. In embodiments, the condensation reaction between the suitable diacid and the tris(hydroxymethyl)aminomethane may be performed at a reduced pressure, such as less than about 100 mmHg, or in the range of from about 0.1 mmHg to about 50 mmHg, at a suitable temperature to ensure complete reaction, such as in the temperature range of from about 120° C. to about 220° C., or from about 130° C. to about 210° C., or from about 150° C. to about 210° C. The condensation reaction may be carried out with or without the use of a catalyst; however catalysts may be used to expedite the completion of the reaction. The various types of catalysts that can be used include, for example, tetraalkyl titanates, dialkyltin oxides such as dibutyltin oxide (dibutyl oxostannane), tetraalkyltin oxide compounds such as dibutyltin dilaurate, dialkylstannoic acid compounds such as butylstannoic acid, aluminum alkoxides, alkyl zinc, dialkyl zinc, zinc oxide, stannous oxide, or mixtures thereof; and which catalysts are selected in amounts of, for example, from about 0.005 mole percent to about 5 mole percent based on the starting diacid. In embodiments, the condensation reaction is complete (i.e., at least 95%, such as 99%, of the diacid has been reacted) in less than about 15 hours, such as less than about 12 hours, or less than about 10 hours.

As an example, the dimer oxazoline tetra-alcohol with $R_1$ equal to —$(CH_2)_n$— wherein n=10, may be prepared from the high-temperature condensation of 1,12-dodecanedioic acid with 2 molar equivalents of tris(hydroxymethyl)-aminomethane, as depicted in the General Scheme 1 (below), where $R_1$ may be defined as set forth above with respect to General Formula I.

General Scheme 1

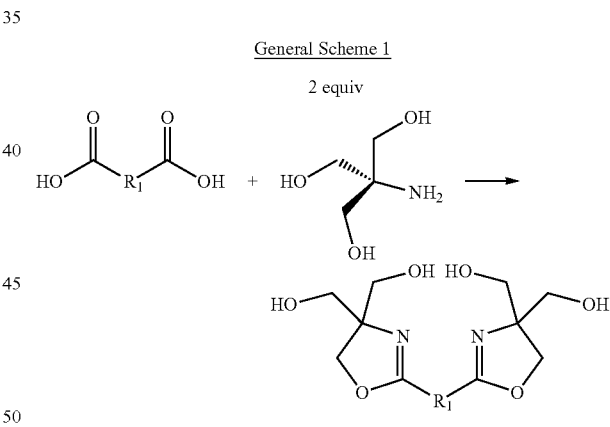

The product of this reaction may be purified by recrystallization in a suitable organic solvent, for example, simple alcohol solvents such as methanol, ethanol or iso-propanol, or combinations of polar organic solvents with non-polar organic solvents, such as for example the use of ethyl acetate with n-hexane in a volume ratio of respectively, from about 0.1 parts to 5 parts ethyl acetate to about 1 part to about 20 parts n-hexane. It is a preferred embodiment that the product of General Scheme I is purified before proceeding onto a second chemical transformation, which may include, for example, esterification of the tetra-alcohol, formation of urethane groups from the tetra-alcohol, etherification of the tetra-alcohol, or various other chemical transformations.

Esterification of the tetra-alcohol may be accomplished by several reaction methods known in the art, including by direct condensation with a monocarboxylic acid. For example, the tetra-ester of Formula I', wherein all of the groups $R_2$, $R_2'$, $R_3$ and $R_3'$ are the same acyl groups, can be readily prepared by condensation with at least 4 molar equivalents of a desired monocarboxylic acid carried out in the absence of solvent, at a suitable high temperature to ensure complete reaction (such as above about 150° C., or in the range of from about 150° C. to about 250° C.) and under ambient pressure. As an example, when the tetra-esterification is accomplished by direct condensation with 4 molar equivalents of lauric acid (dodecanoic acid), the product obtained is the dodecanoate tetra-ester of the starting dimer-oxazoline tetra-alcohol.

In further embodiments, when the esterification of the dimer-oxazoline of General Formula I' is carried out with an excess amount of an aromatic monocarboxylic acid (such as 4-methoxybenzoic acid) to afford the tetra-ester, one or more oxazoline products may be obtained in a reproducible manner (proven by HPLC-MS analysis). The mixture of products includes the dimer oxazoline tetra-(4-methoxybenzoate) ester as a product, and aromatic mono-oxazoline products among the major products, such as 4-methoxyphenyloxazoline compounds. An ink composition including such a mixture of one or more substituted dimer oxazoline and aromatic oxazoline compounds and/or derivatives has desirable rheological properties for use in solid phase change inkjet ink compositions, and provides robust and durable prints.

In further embodiments, the preparation of substituted aromatic mono-oxazoline compounds and/or derivatives may be accomplished by direct condensation reaction between an aromatic monocarboxylic acid and a suitable aminoalcohol, at temperatures that are reduced from the equivalent condensation involving an alkane carboxylic acid. For example, an aromatic mono-oxazoline diester compound can be prepared by condensation reaction between three molar equivalents of 4-methoxybenzoic acid and one equivalent of tris(hydroxymethyl)-aminomethane carried out at a reduced temperature, such as less than about 180° C., or in the range of from about 150° C. to about 180° C. Due the conjugation of the phenyl group with the oxazoline imine moiety in the oxazoline product, the thermal activation energy required for this condensation reaction is reduced, and therefore the aromatic oxazoline compound is produced at lower reaction temperatures.

In embodiments, derivatives of the dimer-oxazoline compounds shown in Formula I' can be ester derivatives, wherein one or more groups $R_2$, $R_2'$, $R_3$ and $R_3'$ are acyl groups, such as a group of the general formula —(C═O)—$(CH_2)_n$$CH_3$, wherein n is either zero or an integer of from 1 to about 50, such as an integer of from about 4 to about 30, or an integer of from about 8 to about 16; or an alkylaryl group, such as one of the general formula

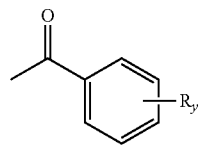

wherein $R_y$ is H, OH, $OCH_3$, Cl, Br, F, I, $NH(COCH_3)$, $CH_3$, $CH_2CH_3$, isopropyl, t-butyl, $CO_2CH_3$, $CO_2H$, an alkyl group having from 1 to about 18 carbons or from about 2 to about 66 carbons, or alkoxy group having from 1 to about 8 carbons or from about 2 to about 6 carbons.

The formation of urethane groups from the tetra-alcohol may be accomplished by several reaction methods known in the art. For example, compounds of General Formula I' in which all of the groups $R_2$, $R_2'$, $R_3$ and $R_3'$ have the general formula —(C═O)—NH—Rz (where $R_z$ is either a linear alkyl group of the formula —$(CH_2)_n$$CH_3$ wherein n is either zero or an integer of from 1 to about 36, such as an integer of from 2 to about 24, or an integer of from about 5 to about 20, or where $R_z$ is an alkylaryl group containing from about 6 to about 20 carbon atoms, such as from about 7 to about 18 carbon atoms, or from about 7 to about 14 carbon atoms) can be readily prepared by reacting the tetra-alcohol with a stoichiometric amount of a desired monofunctional or multifunctional isocyanate reactant, in the presence of a suitable solvent, which may optionally be the isocyanate reactant itself (i.e. in the absence of a co-solvent). The isocyanate reactant can be any desired material which contains at least one —N═C═O functional group, bonded to one or more groups that are either an alkyl group that can be either linear, cyclic or branched, aryl group, alkylaryl group, arylalkyl group, alkylene group, alkyleneoxy group, or combinations thereof. Examples of commonly used monofunctional, difunctional or multifunctional isocyanate reactants may include those of the general formula $R_{15}(NCO)_p$ wherein $R_{15}$ is (i) an alkyl or alkylene group (including linear and branched, saturated and unsaturated, cyclic and acyclic, and substituted and unsubstituted alkyl and alkylene groups, and wherein heteroatoms, such as oxygen, nitrogen, sulfur, silicon, phosphorus, and the like either may or may not be present in the alkyl or alkylene group), in one embodiment with at least about 8 carbon atoms, in another embodiment with at least about 10 carbon atoms, and in yet another embodiment with at least about 12 carbon atoms, and in one embodiment with no more than about 60 carbon atoms, in another embodiment with no more than about 50 carbon atoms, and in yet another embodiment with no more than about 40 carbon atoms, (ii) an aryl or arylene group (including substituted and unsubstituted aryl and arylene groups, and wherein heteroatoms, such as oxygen, nitrogen, sulfur, silicon, phosphorus, and the like either may or may not be present in the aryl or arylene group), in one embodiment with at least about 5 carbon atoms, and in another embodiment with at least about 6 carbon atoms, and in one embodiment with no more than about 50 carbon atoms, in another embodiment with no more than about 25 carbon atoms, and in yet another embodiment with no more than about 12 carbon atoms, (iii) an arylalkyl or arylalkylene group (including substituted and unsubstituted arylalkyl and arylalkylene groups, wherein the alkyl portion of the arylalkyl or arylalkylene group can be linear or branched, saturated or unsaturated, cyclic or acyclic, and substituted or unsubstituted, and wherein heteroatoms, such as oxygen, nitrogen, sulfur, silicon, phosphorus, and the like either may or may not be present in either the aryl or the alkyl portion of the arylalkyl or arylalkylene group), in one embodiment with at least about 6 carbon atoms, and in another embodiment with at least about 7 carbon atoms, and in one embodiment with no more than about 60 carbon atoms, in another embodiment with no more than about 40 carbon atoms, and in yet another embodiment with no more than about 30 carbon atoms, or (iv) an alkylaryl or alkylarylene group (including substituted and unsubstituted alkylaryl and alkylarylene groups, wherein the alkyl portion of the alkylaryl or alkylarylene group can be linear or branched, saturated or unsaturated, cyclic or acyclic, and substituted or unsubstituted, and wherein heteroatoms, such as oxygen, nitrogen, sulfur, silicon, phosphorus, and the like either may or may not be present in either the aryl or the alkyl portion of the alkylaryl or alkylarylene group), in one embodiment with at least about 6 carbon atoms, and in another embodiment with at least about 7 carbon atoms, and in one embodiment with no more than about 60 carbon atoms, in another embodiment with no more than about 40 carbon atoms, and in yet another embodiment with no more than about 30 carbon atoms, although the number of carbon atoms can be outside of these ranges, wherein the substituents on the substituted alkyl, alkylene, aryl, arylene, arylalkyl, arylalkylene, alkylaryl, and alkylarylene groups may be halogen atoms, cyano groups, ether groups, aldehyde groups, ketone groups, ester groups, carbonyl groups, thiocarbonyl groups, mercapto groups, nitro groups, nitroso groups, sulfone groups, acyl groups, mixtures thereof, and the like, and p is an integer representing the number of isocyanate groups, being, for example, 1, 2, 3, or the like in the instance of monomeric isocyanates and having no necessary upper limit in the case of multifunctional isocyanate reactants.

Examples of monoisocyanates may include octadecylisocyanate; hexadecylisocyanate; octylisocyanate; n-butyl and t-butylisocyanate; cyclohexyl isocyanate; adamantyl isocyanate; ethylisocyanatoacetate; ethoxycarbonylisocyanate; phenylisocyanate; alphamethylbenzyl isocyanate; 2-phenylcyclopropyl isocyanate; benzylisocyanate; 2-ethylphenylisocyanate; benzoylisocyanate; meta and para-tolylisocyanate; 2-, 3-, or 4-nitrophenylisocyanates; 2-ethoxyphenyl isocyanate; 3-methoxyphenyl isocyanate; 4-methoxyphenylisocyanate; ethyl 4-isocyanatobenzoate; 2,6-dimethylphenylisocyante; 1-naphthylisocyanate; (naphthyl)ethylisocyantes; and the like, as well as mixtures thereof. Examples of diisocyanates may include isophorone diisocyanate (PDT); toluene diisocyanate (TDI); diphenylmethane-4,4'-diisocyanate (MDI); hydrogenated diphenylmethane-4,4'-diisocyanate (H12MDI); tetra-methyl xylene diisocyanate (TMXDI); hexamethylene-1,6-diisocyanate (HDI); naphthalene-1,5-diisocyanate; 3,3'-dimethoxy-4,4'-biphenyldiisocyanate; 3,3'-dimethyl-4,4'-bimethyl-4,4'-biphenyldiisocyanate; phenylene diisocyanate; 4,4'-biphenyldiisocyanate; 2,2,4-trimethylhexamethylene diisocyanate and 2,4,4-trimethylhexamethylene diisocyanate, tetramethylene xylene diisocyanate; 4,4'-methylenebis(2,6-diethylphenyl isocyanate); 1,12-diisocyanatododecane; 1,5-diisocyanato-2-methylpentane; 1,4-diisocyanatobutane; C-36 dimer diisocyanate and cyclohexylene diisocyanate and its isomers such as 1,3-bis[isocyanatomethylcyclohexane]; uretidione dimers of HDI; and the like, as well as mixtures thereof. Examples of triisocyanates or their equivalents include the trimethylolpropane trimer of TDI, and the like, isocyanurate trimers of TDI, IPDI, and the like, and biuret trimers of TDI, HDI, IPDI, and the like, as well as mixtures thereof.

The reaction between the oxazoline alcohol groups and the isocyanate reactant can be performed at a suitable temperature to ensure complete reaction, such as in the temperature range of from about −50° C. to about 150° C., or from about −20° C. to about 100° C., or from about 0° C. to about 80° C. These reactions can be carried out with or without the use of a catalyst; however catalysts are preferably used to expedite the completion of the reaction. The various types of catalysts that can be used include Lewis acid catalysts comprising tin including dialkyltin oxides, such as dibutyltin oxide (dibutyl oxostannane), tetraalkyltin oxide compounds such as dibutyltin dilaurate, and dialkylstannoic acid compounds such as butylstannoic acid and stannous octoate, bismuth tris-neodecanoate, cobalt benzoate, lithium acetate, triethylamine, ferric chloride, aluminum trichloride, boron trichloride, boron trifluoride, titanium tetrachloride, and tetraalkyl titanates such as titanium tetra-isopropoxide, and the like. The amount of catalyst required for the reaction of the oxazoline alcohol groups (assumed to be the limiting reactant) and the isocyanate reactant can be in the range of from about 0.0001 molar equivalents to about 0.10 molar equivalents based on the limiting reactant, or from about 0.001 molar equivalents to about 0.05 molar equivalents, or from about 0.005 molar equivalents to about 0.05 molar equivalents, however the actual amount of catalyst used can also be outside of these ranges.

In embodiments, compounds of General Formula I' may have urethane groups for groups $R_2$, $R_2'$, $R_3$ and $R_3'$. For example, one or more of $R_2$, $R_2'$, $R_3$ and $R_3'$ in the General Formula I' may be a group of the general formula —(C=O)—NH—$R_z$ where $R_z$ is either a linear alkyl group of the formula —$(CH_2)_n CH_3$ wherein n is either zero or an integer of from 1 to about 36, such as an integer of from 2 to about 24, or an integer of from about 5 to about 20, or where $R_z$ is an alkylaryl group containing from about 6 to about 20 carbon atoms, such as from about 7 to about 18 carbon atoms, or from about 7 to about 14 carbon atoms.

Substituted Oxazoline Compounds and/or Substituted Oxazoline Derivatives Represented by a Compound of "General Formula II."

In embodiments, the one or more substituted oxazoline compounds and/or substituted oxazoline derivatives may be represented by General Formula II having the general structure:

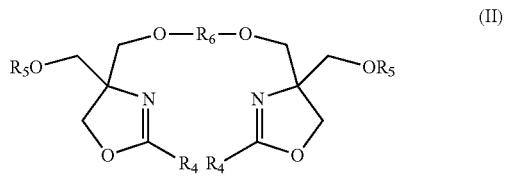

wherein $R_4$ is an alkyl group, aryl group, alkylaryl group, or an aromatic group (each of which may or may not be substituted), such as an alkyl group containing from about 1 to about 60 carbon atoms, such as from about 5 to about 36 carbon atoms, or from about 5 to about 25 carbon atoms, or an aryl group, alkylaryl group, aromatic group containing from about 5 to about 20 carbon atoms, such as from about 6 to about 18 carbon atoms, or from about 7 to about 14 carbon atoms;

$R_6$ is an alkylene group, arylene group, alkylarylene group, or alkylarylene group, or may be defined as the same groups as described earlier for $R_1$ for General Formula I (above). In embodiments, $R_6$ may a branched alkylene group, such as for example a group of the general formula $C_{36}H_{64+n}$ and which may include unsaturated groups and cyclic groups, wherein n is an integer of 0, 1, 2, 3, 4, 5, 6, 7, 8, 9, or 10, including, for example, structural isomers of the general formula

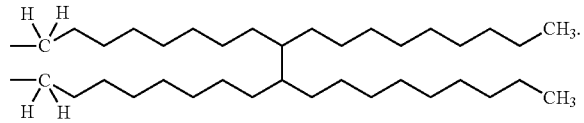

or $R_6$ may be of the general formula

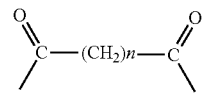

or derived therefrom, in which n is an integer in a range from about 1 to about 35, or from about 2 to about 24; or $R_6$ may be one or more of the following disubstituted aryl diacyl groups with the following formulae:

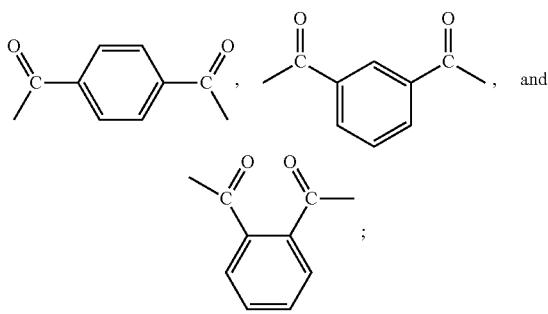

and $R_5$ is an alkyl group, aryl group, alkylaryl group, aromatic group (each of which may or may not be substituted), or a hydrogen, such as an alkyl group containing from about 1 to about 60 carbon atoms, such as from about 5 to about 36 carbon atoms, or from about 5 to about 25 carbon atoms, or an aryl group, alkylaryl group, aromatic group containing from about 5 to about 20 carbon atoms, such as from about 6 to about 18 carbon atoms, or from about 7 to about 14 carbon atoms, or such as a lower alkyl having from 1 to about 12 carbons or from about 2 to about 10 carbons; or an acyl group, such as a group of the general formula $-(C=O)-(CH_2)_n CH_3$, wherein n is either zero or an integer of from 1 to about 50, such as an integer of from about 4 to about 30, or an integer of from about 8 to about 16; or an alkylaryl group, such as, for example, a group of the general formula

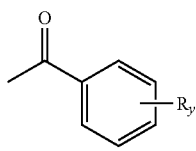

wherein $R_y$ is H, OH, $OCH_3$, Cl, Br, F, I, $NH(COCH_3)$, $CH_3$, $CH_2CH_3$, isopropyl, t-butyl, $CO_2CH_3$, $CO_2H$, an alkyl group having from 1 to about 18 carbons or from about 2 to about 6 carbons, or alkoxy group having from 1 to about 8 carbons or from about 2 to about 6 carbons, or $-(C=O)-NH-R_z$, where $R_z$ is either a linear alkyl group of the formula $-(CH_2)_n CH_3$ wherein n is either zero or an integer of from 1 to about 36, such as an integer of from 2 to about 24, or an integer of from about 5 to about 20, or where $R_1$ is an alkylaryl group containing from about 6 to about 20 carbon atoms, such as from about 7 to about 18 carbon atoms, or from about 7 to about 14 carbon atoms.

In embodiments, the $R_4$ groups may be the same as each other; in other embodiments, the $R_4$ groups may be different from each other. In embodiments, each $R_4$ group may be the same or different so as to give either symmetrical or unsymmetrical structures, depending on the identity of each $R_5$ group (i.e., whether each $R_5$ group is the same or different). In embodiments, the $R_5$ groups may be the same as each other; in other embodiments, the $R_5$ groups may be different from each other. In embodiments, each $R_5$ group may be the same or different so as to give either symmetrical or unsymmetrical structures, depending on the identity of each $R_4$ group (i.e., whether each $R_4$ group is the same or different).

The compounds of General Formula II may be prepared by a condensation process involving a mono-oxazoline diol of Formula A having the general structure:

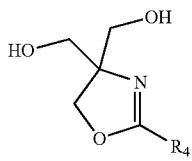

and the appropriate dicarboxylic acid. The general synthesis for a compound of General Formula A is shown in General Scheme 2 (below):

General Scheme 2

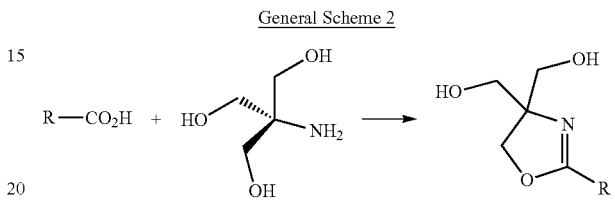

The general synthesis for an exemplary compound of General Formula II is shown in General Scheme 3 (below) in which $R_5$ is H, and $R_4$ and $R_6$ are defined as set forth above with respect to General Formula II:

General Scheme 3

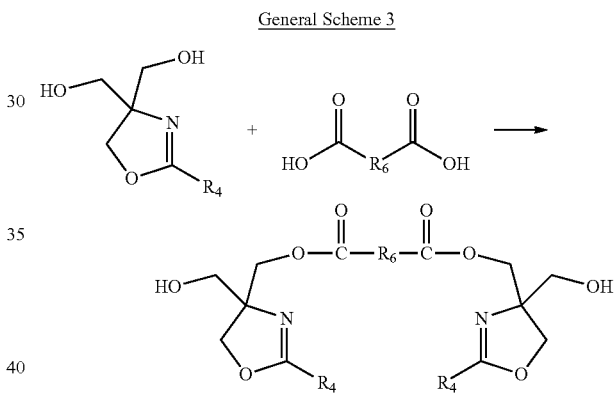

The condensation of general scheme 3 may predominately yield a dimer-oxazoline if it is carried out using at least a two-fold excess or greater of the mono-oxazoline diol precursor.

In embodiments, the condensation involves two esterification reactions, and may be performed at a suitable temperature to ensure complete reaction, such as in the temperature range of from about 120° C. to about 220° C., or from about 130° C. to about 210° C., or from about 150° C. to about 200° C. The condensation reaction may be carried out with or without the use of a catalyst; however catalysts may be used to expedite the completion of the reaction. The various types of catalysts that can be used include, for example, tetraalkyl titanates, dialkyltin oxides such as dibutyltin oxide (dibutyl oxostannane), tetraalkyltin oxide compounds such as dibutyltin dilaurate, dialkylstannoic acid compounds such as butylstannoic acid, aluminum alkoxides, alkyl zinc, dialkyl zinc, zinc oxide, stannous oxide, or mixtures thereof; and which catalysts are selected in amounts of, for example, from about 0.005 mole percent to about 5 mole percent based on the starting diacid. In embodiments, the condensation (esterification) reaction is complete (i.e., at least 95%, such as 99%, of the diacid has been reacted) in less than about 15 hours, such as less than about 12 hours, or less than about 10 hours.

If the relative stoichiometries of the mono-oxazoline diol and the dicarboxylic acid are less than 2:1, such as in the range from about 0.50-1.80:1 of mono-oxazoline diol to dicarboxylic acid, or from about 0.75-1.50:1 of mono-oxazoline diol to dicarboxylic acid, or about 1:1 mono-oxazoline diol to dicarboxylic acid, then oligo-esters and polyesters of General Formula III (below) may result, particularly if performed under conditions of extended reaction times, high temperatures and/or reduced pressure.

Substituted Oxazoline Compounds and/or Substituted Oxazoline Derivatives Represented by a Compound of "General Formula III"

In embodiments, the one or more substituted oxazoline compounds and/or substituted oxazoline derivatives may be represented by General Formula III:

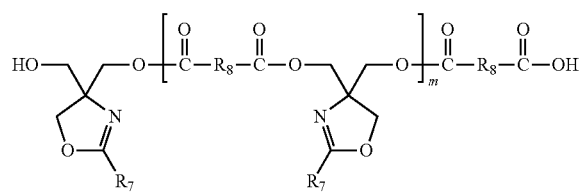
(III)

wherein $R_7$ is an alkyl group, aryl group, alkylaryl group, aromatic group (each of which may or may not be substituted), or may be defined as the same groups as described for $R_4$ for General Formula II;
$R_8$ is an alkylene group, arylene group, arylalkylene group, or alkylarylene group,

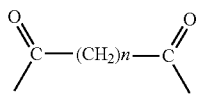

in which n is an integer in a range from about 6 to about 36,

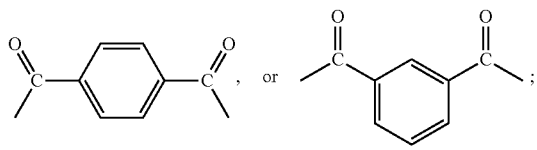

or may be defined as the same groups as described for $R_6$ for General Formula II; and m is an integer of from 1 to about 100, such as from about 1 to about 60, or from about 2 to about 30.

Alternatively, in embodiments, the one or more substituted oxazoline compounds and/or substituted oxazoline derivatives may be represented by General Formula III' in which at least two different repeat structures are present, as illustrated in the General Formula III':

where $R_8$ and $R_8'$ are defined as set forth above for $R_8$ of General Formula III, and may or may not be the same; and group $R_{14}$ is an alkyl, aryl, alkylaryl, arylalkyl, alkylene, and can be linear, branched or cyclic; and where integers m and p can be from 1 to about 50, or from 1 to about 30, or from 1 to about 20.

As stated above, if the relative stoichiometries of the mono-oxazoline diol and dicarboxylic acid are less than 2:1, such as in the range from about 0.50-1.80:1 of mono-oxazoline diol to dicarboxylic acid, or from about 0.75-1.50:1 of mono-oxazoline diol to dicarboxylic acid, or about 1:1 mono-oxazoline diol to dicarboxylic acid, then oligo-esters and polyesters of General Formula III may result, particularly if performed under conditions of extended reaction times, high temperatures and/or reduced pressure. In embodiments, oligo-esters and polyesters of General Formula III may be obtained by a condensation reaction performed at a reduced pressure, such as less than about 100 mmHg, or in the range of from about 0.1 mmHg to about 50 mmHg, at a suitable high temperature to ensure complete reaction, such as in the temperature range of from about 120° C. to about 250° C., or from about 130° C. to about 230° C., or from about 150° C. to about 220° C. The condensation reaction may be carried out with or without the use of a catalyst; however catalysts may be used to expedite the completion of the reaction. The various types of catalysts that can be used include, for example, tetraalkyl titanates, dialkyltin oxides such as dibutyltin oxide (dibutyl oxostannane), tetraalkyltin oxide compounds such as dibutyltin dilaurate, dialkylstannoic acid compounds such as butylstannoic acid, aluminum alkoxides, alkyl zinc, dialkyl zinc, zinc oxide, stannous oxide, or mixtures thereof; and which catalysts are selected in amounts of, for example, from about 0.005 mole percent to about 5 mole percent based on the starting diacid. In embodiments, oligo-esters and polyesters of General Formula III may be obtained by a condensation reaction in which the reaction time is greater than 4 hours, such as a reaction time in the range of from about 4 hours to about 24 hours, or from about 5 hours to about 20 hours.

Substituted Oxazoline Compounds and/or Substituted Oxazoline Derivatives Represented by a Compound of "General Formula IV."

In embodiments, the one or more substituted oxazoline compounds and/or substituted oxazoline derivatives may be represented by General Formula IV having the general structure:

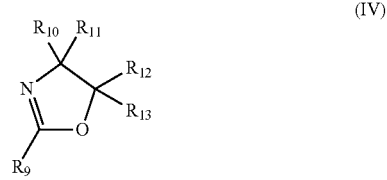
(IV)

wherein $R_9$ is an alkyl group of from about 1 to about 60 carbon atoms, $R_{10}$, $R_{11}$, $R_{12}$, and $R_{13}$ are the same or different and are groups having from about 1 to about 60 carbons, or

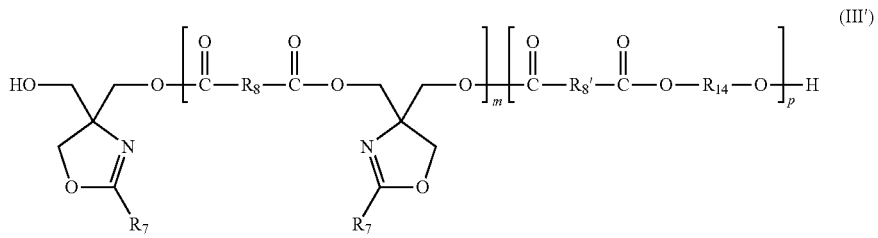
(III')

from about 2 to about 55 carbons, an hydroxyalkyl group having from about 1 to about 60 carbons, or from about 2 to about 55 carbons, or an alkyl ester group having from about 1 to about 60 carbons, or from about 2 to about 55 carbons; for example, $R_{10}$, $R_{11}$ $R_{12}$, and $R_{13}$ may be an hydroxylalkyl group —$(CH_2)_n$—OH, wherein n is an integer of from about 1 to about 60, or from about 2 to about 55, or $R_{10}$, $R_{11}$ $R_{12}$, and $R_{13}$ may be an alkyl ester group —$(CH_2)_n O_2$ C—$(CH_2)_m$ $CH_3$, wherein n is an integer of from about 1 to about 7, or from about 2 to about 5, and m is an integer of from about 1 to about 60.

In other embodiments, in General Formula IV, $R_9$ may be an alkyl group, aryl group, alkylaryl group, or aromatic group (each of which may or may not be substituted), such as an alkyl group containing from about 1 to about 60 carbon atoms, such as from about 5 to about 36 carbon atoms, or from about 5 to about 25 carbon atoms, or an aryl group, alkylaryl group, aromatic group containing from about 5 to about 20 carbon atoms, such as from about 6 to about 18 carbon atoms, or from about 7 to about 14 carbon atoms, or aromatic group, such as, for example,

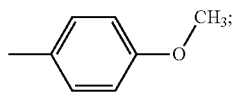

$R_{10}$, $R_{11}$ $R_{12}$, and $R_{13}$ are the same or different and are an hydrogen, halogens such as F, Cl, Br, I, alkyl group, aryl group, alkylaryl group, or aromatic group (each of which may or may not be substituted) as defined for $R_9$, including, for example, a linear or branched alkyl group of from about 1 to about 60 carbons, a linear or branched hydroxylalkyl group of from about 1 to about 60 carbons, a linear or branched alkyl ester group of from about 1 to about 60 carbons, or an aryl ester group, or a cyclic alkyl group of from about 3 to about 60 carbons, a cyclic alkyl alcohol group of from about 3 to about 60 carbons, a cyclic alkyl ester group of from about 3 to about 60 carbons, wherein at least one of $R_9$, $R_{10}$, $R_{11}$ $R_{12}$, and $R_{13}$ is an aromatic group, which may or may not be a substituted aromatic group.

The compounds of General Formula IV may be prepared by a condensation reaction occurring at a suitable temperature, such as a high temperature condensation at a temperature above about 120° C., or in the range of from about 120° C. to about 220° C., or in the range of from about 150° C. to about 210° C., of an acid having an $R_9$ group as defined above with at least 1 molar equivalent of a suitable amino alcohol. In embodiments, the condensation reaction between the desired acid and the suitable amino alcohol may be performed at a reduced pressure, such as less than about 100 mmHg, or in the range of from about 0.1 mmHg to about 50 mmHg, at a suitable temperature to ensure complete reaction, such as in the temperature range of from about 120° C. to about 220° C., or from about 130° C. to about 210° C., or from about 150° C. to about 210° C. The condensation reaction may be carried out with or without the use of a catalyst; however catalysts may be used to expedite the completion of the reaction. The various types of catalysts that can be used include, for example, tetraalkyl titanates, dialkyltin oxides such as dibutyltin oxide (dibutyl oxostannane), tetraalkyltin oxide compounds such as dibutyltin dilaurate, dialkylstannoic acid compounds such as butylstannoic acid, aluminum alkoxides, alkyl zinc, dialkyl zinc, zinc oxide, stannous oxide, or mixtures thereof; and which catalysts are selected in amounts of, for example, from about 0.005 mole percent to about 5 mole percent based on the starting diacid. In embodiments, the condensation reaction is complete (i.e., at least 95%, such as 99%, of the diacid has been reacted) in less than about 15 hours, such as less than about 12 hours, or less than about 10 hours.

Example compounds of General Formula IV may be prepared by the methods described in U.S. Pat. No. 5,817,169 and U.S. Pat. No. 5,698,017, each of which are incorporated herein by reference in their entirety.

Table 1 (below) shows selected examples of mono-oxazoline compounds, and a selection of thermal properties and physical state. Compounds 1-6 of Table 1 are hydroxyalkyl substituted mono-oxazolines and aliphatic esters of hydroalkyl substituted mono-oxazolines, all of which are crystalline and exhibit sharp melting and sharp crystallization temperatures. Compounds 7-11 of Table 1 are the aromatic oxazoline esters, and generally do not exhibit crystalline properties, but are instead amorphous compounds. The examples of mono-oxazoline compounds may be suitable as components of ink compositions, such as phase-change agents, binder resins, compatibilizing agents, synergists, rheology modifiers or plasticizers used in phase change inks for inkjet printing or offset printing inks. Table 2 (below) shows selected examples of dimeric and oligo-/poly-oxazoline compounds.

TABLE 1

Representative examples of mono-oxazoline compounds and their physical properties.

| No. | Mono-Oxazoline compound | $T_{melt}$ (° C.) (DSC) | $T_{cryst}$ (° C.) (DSC) | Physical State (room temp) |
|---|---|---|---|---|
| 1 | | 98 | 72.4 | Crystalline |
| 2 | | 60 | 45 | Crystalline |

TABLE 1-continued
Representative examples of mono-oxazoline compounds and their physical properties.
| No. | Mono-Oxazoline compound | $T_{melt}$ (° C.) (DSC) | $T_{cryst}$ (° C.) (DSC) | Physical State (room temp) |
|---|---|---|---|---|
| 3 | 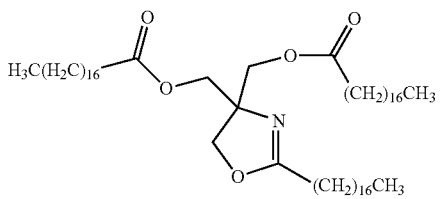 | 56 | 33 | Crystalline |
| 4 | 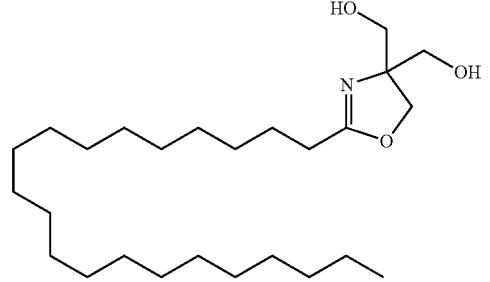 [SMILES: CCCCCCCCCCCCCCCCCCCCCC1=NC(CO)(CO)CO1] | 108.6 | 92 | Crystalline |
| 5 | 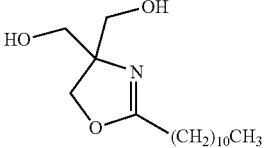 | 97 | 73 | Crystalline |
| 6 | 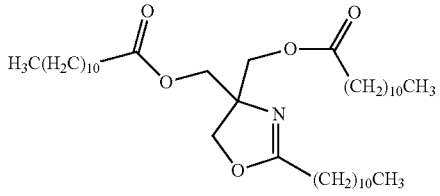 | — | | Crystalline |
| 7 | 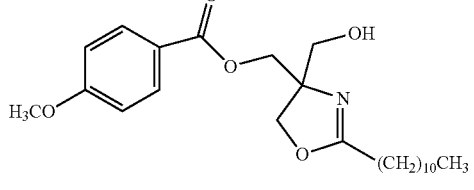 | | | Amorphous |
| 8 | 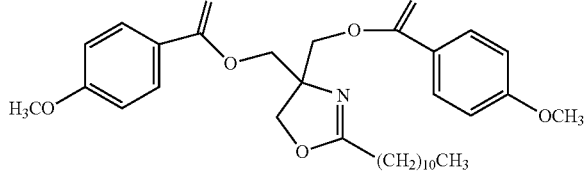 | | | Amorphous |

TABLE 1-continued

Representative examples of mono-oxazoline compounds and their physical properties.

| No. | Mono-Oxazoline compound | $T_{melt}$ (° C.) (DSC) | $T_{cryst}$ (° C.) (DSC) | Physical State (room temp) |
|---|---|---|---|---|
| 9 | | Tg (onset) range from 5 to 15° C. | | Amorphous |
| 10 | | | | Amorphous |
| 11 | | | | Amorphous |

TABLE 2

Representative examples of dimeric and oligo-/poly-oxazoline compounds.

| Entry No. | Oxazoline compound | $R_1$ | $R_2$ ($R_2'$) | $R_3$ ($R_3'$) |
|---|---|---|---|---|
| 1 | Structure: bis-oxazoline with $R_2O$—, $OR_2'$, $R_3O$—, $OR_3'$ substituents and $R_1$ bridge | —$(CH_2)_n$— where n = 2, 4, 8, 10, 12, 16 | H | H |
| 2 | Structure: bis-oxazoline with $R_2O$—, $OR_2'$, $R_3O$—, $OR_3'$ substituents and $R_1$ bridge | —$(CH_2)_n$— where n = 2, 4, 8, 10, 12, 16 | —(C=O)—$(CH_2)_n CH_3$ Where n = 2, 4, 6, 10, 14, and range from 30-50 | —(C=O)—$(CH_2)_n CH_3$ Where n = 2, 4, 6, 10, 14, and range from 30-50 |
| 3 | Structure: bis-oxazoline with $R_2O$—, $OR_2'$, $R_3O$—, $OR_3'$ substituents and $R_1$ bridge | —$(CH_2)_n$— where n = 2, 4, 8, 10, 12, 16 | Acetylphenyl group with $R_y$ substituent where $R_y$ = H, OH, $OCH_3$, Cl, Br, F, I, $NH(COCH_3)$, $CH_3$, isopropyl, t-butyl, $CO_2CH_3$, $CO_2H$, $(CH_2)_m CH_3$ where integer m is 1 to 17, and $O(CH_2)_p CH_3$ where integer p is 1 to 7. | Acetylphenyl group with $R_y$ substituent where $R_y$ = H, OH, $OCH_3$, Cl, Br, F, I, $NH(COCH_3)$, $CH_3$, isopropyl, t-butyl, $CO_2CH_3$, $CO_2H$, $(CH_2)_m CH_3$ where integer m is 1 to 17, and $O(CH_2)_p CH_3$ where integer p is 1 to 7. |

TABLE 2-continued
Representative examples of dimeric and oligo-/poly-oxazoline compounds.
| Entry No. | Oxazoline compound | $R_1$ | $R_2 (R_2')$ | $R_3 (R_3')$ |
|---|---|---|---|---|
| 4 | 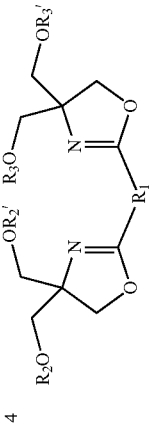 | $C_{36}H_{64+n}$ branched alkylene group, including structural isomer (below) 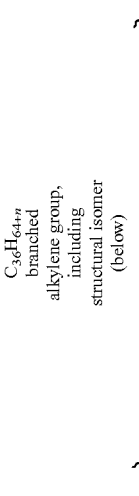 | H | H |

TABLE 2-continued
Representative examples of dimeric and oligo-/poly-oxazoline compounds.
| Entry No. | Oxazoline compound | $R_1$ | $R_2$ ($R_2'$) | $R_3$ ($R_3'$) |
|---|---|---|---|---|
| 5 | 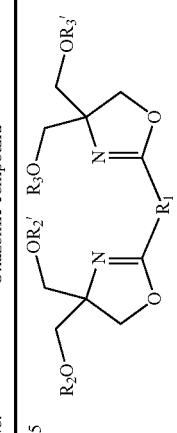 | $C_{36}H_{64+n}$ branched alkylene group, including structural isomer (below) | —(C=O)—(CH$_2$)$_n$CH$_3$ Where n = 2, 4, 6, 10, 14, and range from 30-50 | —(C=O)—(CH$_2$)$_n$CH$_3$ Where n = 2, 4, 6, 10, 14, and range from 30-50 |

TABLE 2-continued

Representative examples of dimeric and oligo-/poly-oxazoline compounds.

| Entry No. | Oxazoline compound | $R_1$ | $R_2$ ($R_2'$) | $R_3$ ($R_3'$) |
|---|---|---|---|---|
| 6 |  | $C_{36}H_{64-n}$ branched alkylene group, including structural isomer (below)<br>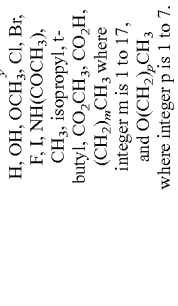 | <br>where $R_y$ = H, OH, OCH$_3$, Cl, Br, F, I, NH(COCH$_3$), CH$_3$, isopropyl, t-butyl, CO$_2$CH$_3$, CO$_2$H, (CH$_2$)$_m$CH$_3$ where integer m is 1 to 17, and O(CH$_2$)$_p$CH$_3$ where integer p is 1 to 7. | <br>where $R_y$ = H, OH, OCH$_3$, Cl, Br, F, I, NH(COCH$_3$), CH$_3$, isopropyl, t-butyl, CO$_2$CH$_3$, CO$_2$H, (CH$_2$)$_m$CH$_3$ where integer m is 1 to 17, and O(CH$_2$)$_p$CH$_3$ where integer p is 1 to 7. |
| 7 | 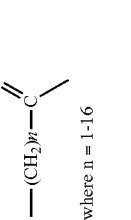 | —(CH$_2$)$_n$CH$_3$ where n = 1-17 |  where n = 1-16 | H |

TABLE 2-continued

Representative examples of dimeric and oligo-/poly-oxazoline compounds.

| Entry No. | Oxazoline compound | $R_1$ | $R_2 (R_2')$ | $R_3 (R_3')$ |
|---|---|---|---|---|
| 8 | Bis-oxazoline with $OR_5$, $R_5O$, $R_6$ linker, $R_4$ substituents | $-(CH_2)_n CH_3$ where n = 1-17 | Diacyl linker $-C(=O)-(CH_2)_n-C(=O)-$ where n = 1-16 | Acetyl-substituted phenyl where $R_y =$ H, OH, OCH$_3$, Cl, Br, F, I, NH(COCH$_3$), CH$_3$, isopropyl, t-butyl, CO$_2$CH$_3$, CO$_2$H, (CH$_2$)$_m$CH$_3$ where integer m is 1 to 17, and O(CH$_2$)$_p$CH$_3$ where integer p is 1 to 7. |
| 9 | Bis-oxazoline with $OR_5$, $R_5O$, $R_6$ linker, $R_4$ substituents | $-(CH_2)_n CH_3$ where n = 1-17 | Diacyl linker $-C(=O)-(CH_2)_n-C(=O)-$ where n = 1-16 | $-(C=O)-(CH_2)_n CH_3$ Where n = 2, 4, 6, 10, 14, and range from 30-50 |
| 10 | Bis-oxazoline with $OR_5$, $R_5O$, $R_6$ linker, $R_4$ substituents | Substituted phenyl where $R_y =$ H, OH, OCH$_3$, Cl, Br, F, I, NH(COCH$_3$), CH$_3$, isopropyl, t-butyl, CO$_2$CH$_3$, CO$_2$H, (CH$_2$)$_2$CH$_3$ | Diacyl linker $-C(=O)-(CH_2)_n-C(=O)-$ where n = 1-16 | H |

TABLE 2-continued

Representative examples of dimeric and oligo-/poly-oxazoline compounds.

| Entry No. | Oxazoline compound | $R_1$ | $R_2$ ($R_2'$) | $R_3$ ($R_3'$) |
|---|---|---|---|---|
| 11 | (structure with two oxazoline rings linked via $R_5O$–, $R_6$–O, $OR_5$, $R_4$) | Phenyl with $R_y$ = H, OH, OCH$_3$, Cl, Br, F, I, NH(COCH$_3$), CH$_3$, isopropyl, t-butyl, CO$_2$CH$_3$, CO$_2$H, (CH$_2$)$_2$CH$_3$ | $-(C=O)-(CH_2)_n-C(=O)-$ where n = 1-16 | Phenyl with $R_y$ = H, OH, OCH$_3$, Cl, Br, F, I, NH(COCH$_3$), CH$_3$, isopropyl, t-butyl, CO$_2$CH$_3$, CO$_2$H, (CH$_2$)$_2$CH$_3$ |
| 12 | (structure) | Phenyl with $R_y$ = H, OH, OCH$_3$, Cl, Br, F, I, NH(COCH$_3$), CH$_3$, isopropyl, t-butyl, CO$_2$CH$_3$, CO$_2$H, (CH$_2$)$_2$CH$_3$ | $-(C=O)-(CH_2)_n-C(=O)-$ where n = 1-16 | $-(C=O)-(CH_2)_n CH_3$ Where n = 2, 4, 6, 10, 14, and range from 30-50 |
| 13 | (structure) | $-(CH_2)_n CH_3$ where n = 1-17 | 1,4-phenylene diketone (para-C$_6$H$_4$ with two C(=O)– groups) | H |
| 14 | (structure) | $-(CH_2)_n CH_3$ where n = 1-17 | 1,4-phenylene diketone (para-C$_6$H$_4$ with two C(=O)– groups) | $-(C=O)-(CH_2)_n CH_3$ Where n = 2, 4, 6, 10, 14, and range from 30-50 |

TABLE 2-continued

Representative examples of dimeric and oligo-/poly-oxazoline compounds.

| Entry No. | Oxazoline compound | $R_1$ | $R_2 (R_2')$ | $R_3 (R_3')$ |
|---|---|---|---|---|
| 15 | (structure with OR$_5$, R$_6$, N, O, R$_4$) | $-(CH_2)_n CH_3$ where n = 1-17 | (1,3-phenylene diacyl group) | H |
| 16 | (structure with OR$_5$, R$_6$, N, O, R$_4$) | $-(CH_2)_n CH_3$ where n = 1-17 | (1,3-phenylene diacyl group) | $-(C=O)-(CH_2)_n CH_3$ Where n = 2, 4, 6, 10, 14, and range from 30-50 |
| 17 | (structure with OR$_5$, R$_6$, N, O, R$_4$) | $-(CH_2)_n CH_3$ where n = 1-17 | $C_{36}H_{64-n}$, branched alkylene group, including structural isomer (below) | H |

TABLE 2-continued

Representative examples of dimeric and oligo-/poly-oxazoline compounds.

| Entry No. | Oxazoline compound | $R_1$ | $R_2$ ($R_2'$) | $R_3$ ($R_3'$) |
|---|---|---|---|---|
| 18 | 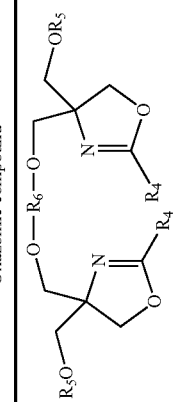 | —(CH$_2$)$_n$CH$_3$ where n = 1-17 | C$_{36}$H$_{64+n}$ branched alkylene group, including structural isomer (below) 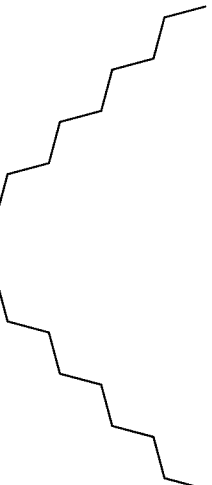 | —(C=O)—(CH$_2$)$_n$CH$_3$ Where n = 2, 4, 6, 10, 14, and range from 30-50 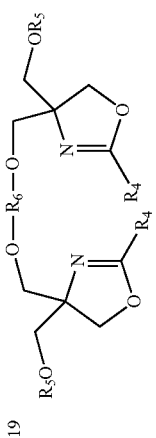 where R$_y$ = H, OH, OCH$_3$, Cl, Br, F, I, NH(COCH3), CH$_3$, isopropyl, t-butyl, CO$_2$CH$_3$, CO$_2$H, (CH$_2$)$_m$CH$_3$ where integer m is 1 to 17, and O(CH$_2$)$_p$CH$_3$ where integer p is 1 to 7. |
| 19 |  | —(CH$_2$)$_n$CH$_3$ where n = 1-17 | 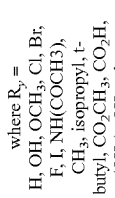 where n = 1-16 | |

TABLE 2-continued
Representative examples of dimeric and oligo-/poly-oxazoline compounds.
| Entry No. | Oxazoline compound | $R_1$ | $R_2$ ($R_2'$) | $R_3$ ($R_3'$) |
|---|---|---|---|---|
| 20 | 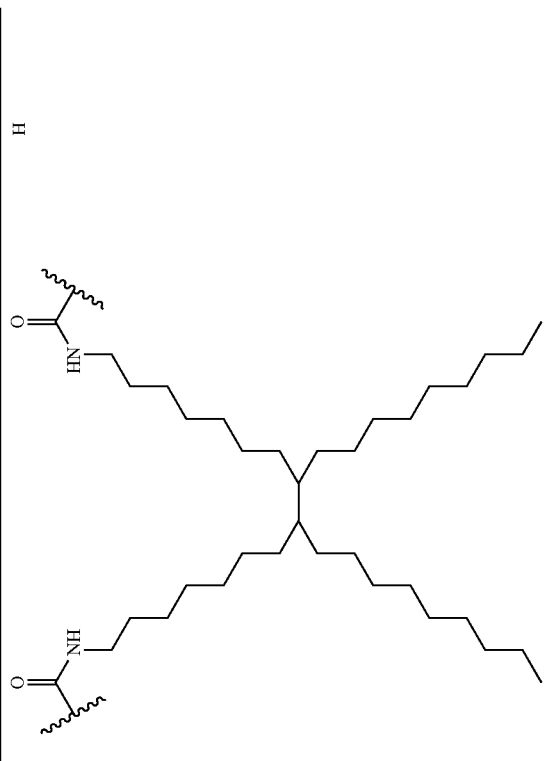 | —$(CH_2)_n$CH$_3$ where n = 1-17 |  | H |
| 21 | | —$(CH_2)_n$— where n = 1-16 | —(C=O)—NH(CH$_2$)$_n$CH$_3$ where n = 5-17 | —(C=O)—NH(CH$_2$)$_n$CH$_3$ where n = 5-17 |

Compositions Comprising Substituted Oxazoline Compounds and/or Substituted Oxazoline Derivatives.

Depending on the nature of the substituent groups, the substituted oxazoline compounds and/or derivatives of the present disclosure may demonstrate crystalline, semi-crystalline or amorphous properties. For example, a compound 3 of Table 2 having General Formula I with $R_1$=—$(CH_2)_{10}$— and $R_2$=H is a highly crystalline compound with very high melting point of approximately 170-175° C. In another example, the substituted mono-oxazoline compound of General Formula IV in Table 1, entry #5 is highly crystalline with melting point of about 97° C., as determined by Differential Scanning calorimetry (DSC) at a scan rate of 10° C./min. The crystallization of this same compound is sharply observed by one of two measurement methods. According to DSC method, using a scan rate of about 10° C./min, the crystallization of compound #5 in Table 1 was determined at about 73° C. However, when the rheological analysis of the same compound is performed on a strain-controlled rheometer instrument, the onset temperature of crystallization was observed at about 88° C. as shown in FIG. 1. (Rheological analysis was performed using a strain-controlled Rheometrics RFS3 instrument, at oscillation frequency of 1 radian/sec (1 Hz) and using a stepwise temperature sweep of about 5° C. temperature increments, starting from 140° C. and cooling down to about room temperature.)

In general, the crystalline oxazoline compounds and/or derivatives of the present disclosure may also have sufficiently low viscosities in the molten state that may enable suitable use as crystalline phase change agent in a solid ink composition for an inkjet printing ink. In embodiments, the crystalline oxazoline compounds and/or derivatives, for example such as the compounds illustrated in Table 1, may have complex viscosities at temperatures above about 110° C. in the range of from about 1 to about 20 cPs (mPa-seconds), or from about 2 to about 15 cPs, or from about 3 to about 13 cPs. At room temperature, the complex viscosity of the crystalline oxazoline compounds and/or derivatives of this disclosure may be about $\geq 1 \times 10^5$ cPs.

Figure 2:
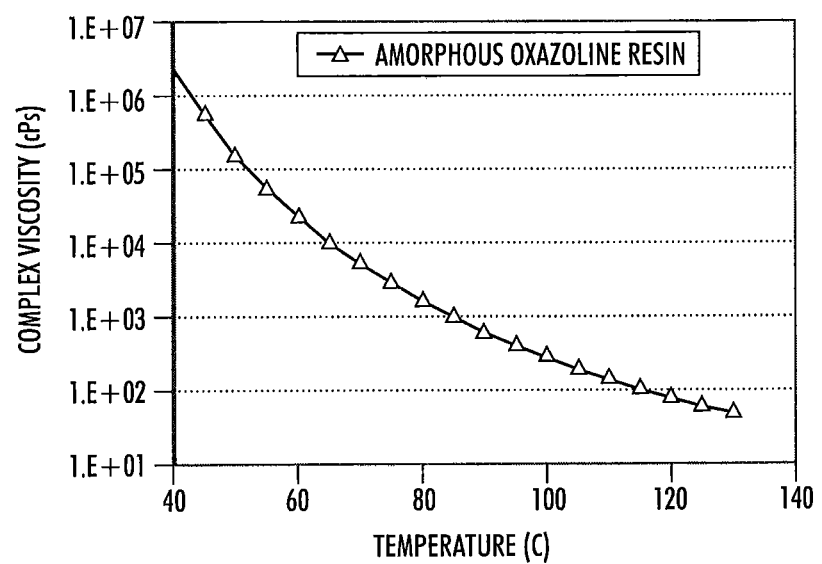
FIG. 2 is an illustration of the rheological profile of an amorphous oxazoline resin (Example 2).

In embodiments, the substituted oxazoline compounds and/or derivatives of the present disclosure may demonstrate amorphous properties, which can be determined by either DSC method or by rheological analysis. For example, the substituted mono-oxazoline compound #9 of Table 1 is amorphous by the fact that it exhibited a glass transition phase (Tg) with onset temperature in the range of from about 5° C. to about 15° C. when analyzed by DSC at a scan rate of 10° C./min. In another example, the composition described in Example 2 which comprises compound #9 of Table 1 as its most abundant constituent, along with minor amounts (<5 wt % each) of the substituted oxazoline compounds #10-11 of Table 1 and compound #3 of Table 2, was analyzed on a strain-controlled rheometer instrument and exhibited a complex viscosity profile plot typical of amorphous compounds, as shown in FIG. 2. (Rheological analysis was performed using a strain-controlled Rheometrics RFS3 instrument, at oscillation frequency of 1 Hz and using a stepwise temperature sweep of about 5° C. temperature increments, starting from 130° C. and cooling down to about room temperature.)

In general, the amorphous oxazoline compounds and/or derivatives of the present disclosure have suitable range of complex viscosities that may enable the use of these compounds in a phase change ink composition for an inkjet printing ink. For example, the amorphous oxazoline compounds and/or derivatives can have viscosities that enable their used as a binder agent, rheology modifier, compatibilizer, synergist for pigment or other additive. In embodiments, the amorphous oxazoline compounds and/or derivatives may have complex viscosities at temperatures above about 110° C. in the range of from about 20 to about, 500 cPs (mPa-seconds), or from about 40 to about 300 cPs, or from about 50 to about 250 cPs. At room temperature, the complex viscosity of the crystalline oxazoline compounds and/or derivatives of this disclosure may be $\geq 1 \times 10^5$ cPs.

Clearly, the substituted oxazoline compounds and/or substituted oxazoline derivatives of the present disclosure are versatile, and depending on nature of the substituent groups, such as molecular structure, chain length, degree of branching and type of substituents, one may observe either crystalline, semi-crystalline or amorphous properties. This ability to tune the rheological characteristics of the some of the substituted oxazoline compounds and/or substituted oxazoline derivatives of this disclosure by the choice of the functional group, such as an ester group, enables the design of solid inks having either crystalline, amorphous or even semi-crystalline properties for use in a coating or printing ink application.

In this regard, the substituted oxazoline compounds and/or substituted oxazoline derivatives of the present disclosure may be employed in a variety of applications and included in the composition of a variety of components (e.g., phase-change agents, binder resins, rheology modifiers, compatibilizing agents, synergists, or plasticizers). For example, oxazoline-based components (e.g., phase-change agents, binder resins, rheology modifiers, compatibilizing agents, synergists, or plasticizers) of the present disclosure may be suitable for use in inks characterized as phase change solid inks.

In embodiments, the phase change inks can be solid inks which have melting points of from about 60° C. to about 130° C., for example from about 65° C. to about 120° C., from about 70° C. to about 115° C., as determined by, for example, by differential scanning calorimetry. In embodiments, the phase change ink has a crystallization point of from about 50° C. to about 120° C., or from about 60 to about 115° C., or from about 65 to about 110° C.

Figure 3:
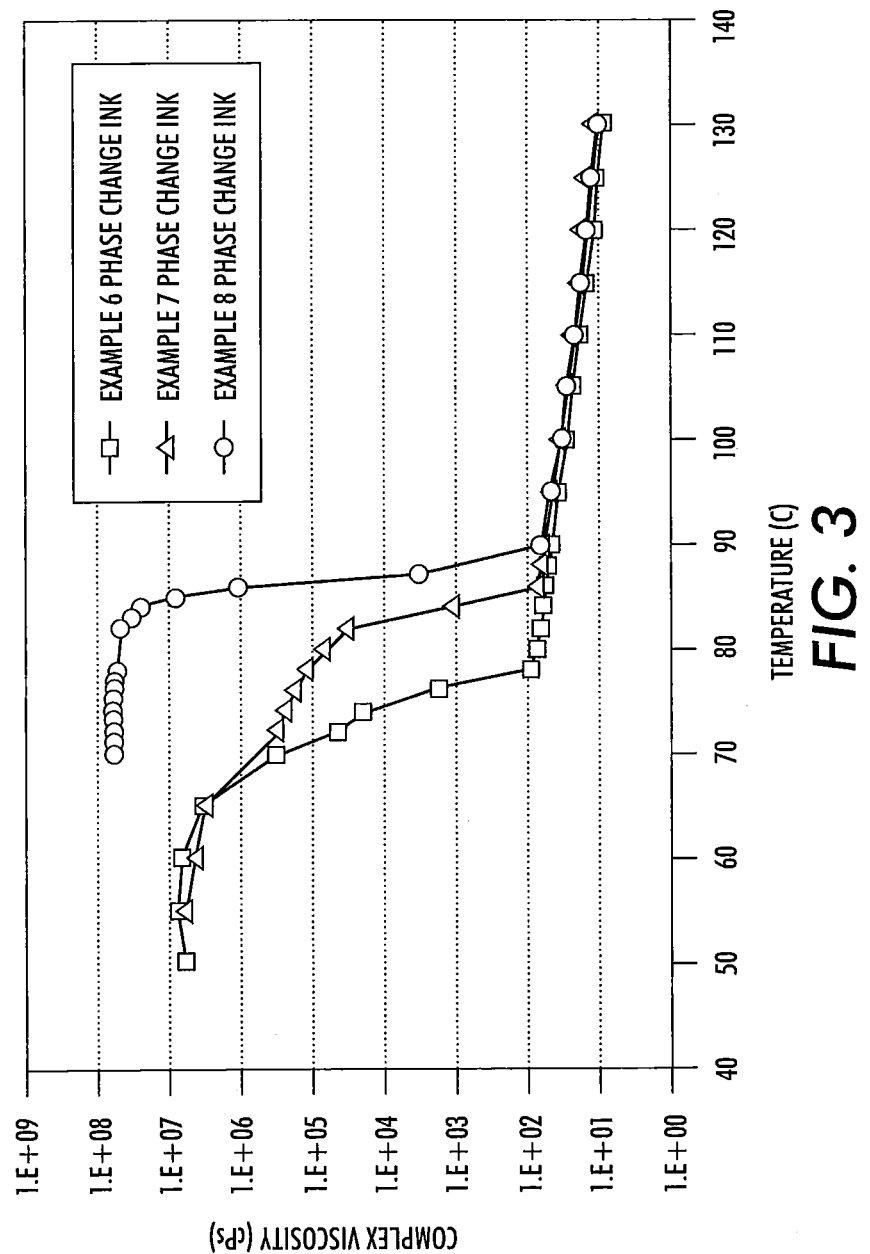
FIG. 3 is an illustration of a comparison of rheological profiles of solid phase change ink compositions comprising one or more oxazoline compounds or derivatives.

In further embodiments, the phase change inks can have a complex viscosity in the molten state, such as for example temperatures above 130° C. in the range of from about 1 to about 20 cPs (centipoise, or mPa-sec), or from about 2 to about 18 cPs, or from about 3 to about 15 cPs. The complex viscosities of the phase change ink can be measured at a range of frequencies, such as from about 1 Hz to about 100 Hz. At room temperature, the phase change ink can have a complex viscosity of about $\geq 1 \times 10^6$ cPs. In embodiments, the phase change inks of Examples 6-8 exhibit phase-change rheological behavior and viscosities in the above disclosed ranges, as shown in FIG. 3.

In embodiments, the substituted oxazoline compounds and/or substituted oxazoline derivatives of the present disclosure may be incorporated into colored or non-colored (or colorless) phase-change ink compositions that include from about 0 to about 30%, or from about 1 to about 20%, or from about 2 to about 15% by weight of dye or pigment. In embodiments, the substituted oxazoline compounds and/or substituted oxazoline derivatives may be present in an amount of from about 1 to about 100%, or from about 25 to about 98%, or from about 50 to about 97% by weight of the phase-change ink composition.

In embodiments, ink compositions of the present disclosure may include a dimer-oxazoline compound or derivative having the general structure of General Formula I in an amount of from about 0.5 to about 60%, such as from about 1 to about 50%, or from about 5 to about 40% by weight of the ink composition.

In embodiments, the ink composition may comprise a dimer-oxazoline compound as an amorphous binder agent or resin having the general structure of General Formula I (which has been converted into an ester, such as aromatic esters, aromatic diesters and/or aliphatic esters) in an amount of from about 0.1 to about 50%, such as from about 1 to about 40%, or from about 2 to about 30% by weight of the ink composition.

In embodiments, the one or more substituted oxazoline compounds and/or substituted oxazoline derivatives present in the composition or present in a specific component (e.g., phase-change agents, binder resins, rheology modifiers or plasticizers) of an ink composition may be a mixture of compounds, where each oxazoline compound or oxazoline derivative may be a compound of General Formula I. In embodiments, a specific component of the ink composition, such as the phase-change agents, binder resins, compatibilizing agents, synergists, rheology modifiers or plasticizers, may include one or more dimer-oxazoline compounds and/or derivatives having the general structure of General Formula I in any desired amount, such as from about 0.5% to about 100%, or from about 10% to about 100%, or from about 30% to about 90% by weight of the respective component (e.g., phase-change agent, binder resin, rheology modifier or plasticizer) present in the ink composition.

In embodiments, the one or more substituted oxazoline compounds and/or substituted oxazoline derivatives present in the composition or present in a specific component of the ink composition (such as phase-change agent, binder resin, compatibilizing agent, synergist, rheology modifier or plasticizer component) may be a mixture of compounds, where each oxazoline compound or oxazoline derivative may be a compound of General Formula II. In embodiments, a specific component of an ink composition, such as the phase-change agent, binder resin, compatibilizing agent, synergist, rheology modifier or plasticizer component, may include one or more dimer-oxazoline compounds and/or derivatives having the general structure of General Formula II in any desired amount, such as from about 0.5% to about 100%, or from about 2% to about 95%, or from about 5% to about 90% by weight of the respective component (e.g., phase-change agent, binder resin, compatibilizing agent, synergist, rheology modifier or plasticizer component) present in the ink composition.

In embodiments, the ink composition includes a substituted dimer-oxazoline compound or derivative having the general structure of General Formula II in any desired amount, such as an amount of from about 1% to about 75%, such as from about 2% to about 65%, or from about 3% to about 50% by weight of the ink composition.

In embodiments, the ink composition comprises a substituted dimer-oxazoline compound as an amorphous binder agent or resin having the general structure of General Formula II (which has been converted into an ester, such as aromatic esters, aromatic diesters and/or aliphatic esters) in any desired amount, such as an amount of from about 1% to about 75%, such as from about 2% to about 65%, or from about 3% to about 50% by weight of the ink composition.

In embodiments, the one or more substituted oxazoline compounds and/or substituted oxazoline derivatives present in the composition or present in a specific component of an ink composition (such as phase-change agent, binder resin, compatibilizing agent, synergist, rheology modifier or plasticizer component) may be a mixture of compounds, where each oxazoline compound or oxazoline derivative may be a compound of General Formula III. In embodiments, a specific component of the ink composition, such as phase-change agent, binder resin, compatibilizing agent, synergist, rheology modifier or plasticizer component, may include one or more dimer-oxazoline compounds and/or derivatives having the general structure of General Formula III in any desired amount, such as from about 1% to about 75%, such as from about 2% to about 65%, or from about 3% to about 50% by weight of the ink composition.

In embodiments, the ink composition includes a substituted oligo-oxazoline compound or derivative having the general structure of General Formula III in any desired amount, such as an amount of from about 1% to about 75%, such as from about 2% to about 65%, or from about 3% to about 50% by weight of the ink composition.

In embodiments, the one or more substituted oxazoline compounds and/or substituted oxazoline derivatives of an exemplary phase-change agent, binder resin, compatibilizing agent, synergist, rheology modifier or plasticizer component may be mixture of one or more of the compounds of the General Formulas I, II, III, and IV. For example, one or more of the compounds of General Formula I may be the major component of a phase-change agent, binder resin, compatibilizing agent, synergist, rheology modifier or plasticizer component; or one or more of the compounds of General Formula II may be the major component of a phase-change agent, binder resin, compatibilizing agent, synergist, rheology modifier or plasticizer component; or one or more of the compounds of General Formula III may be the major component of a phase-change agent, binder resin, compatibilizing agent, synergist, rheology modifier or plasticizer component; or one or more of the compounds of General Formula IV may be the major component of the respective phase-change agent, binder resin, compatibilizing agent, synergist, rheology modifier or plasticizer component.

In embodiments, an ink composition may contain at least two different substituted oxazoline compounds and/or substituted oxazoline derivatives in any desired amount, which may function as the crystalline phase change agent and the amorphous binder agent, wherein the weight-percent ratio between the crystalline phase-change agent (as a substituted oxazoline compounds and/or substituted oxazoline derivatives) and the amorphous binder agent (as a substituted oxazoline compounds and/or substituted oxazoline derivatives) may respectively be from about 90:10 to about 25:75, such as from about 80:20 to about 40:60, or from about 75:25 to about 50:50.

In embodiments, the one or more substituted oxazoline compounds and/or substituted oxazoline derivatives of the amorphous binder agent or resin may be mixture of one or more of the compounds of the General Formulas I, II, III, and IV, which includes at least one ester, such as aromatic esters, aromatic diesters and/or aliphatic esters, of one or more of the compounds of the General Formulas I, II, III, and IV.

In embodiments, the one or more substituted oxazoline compounds and/or substituted oxazoline derivatives of the phase-change agent may be mixture of one or more of the compounds of the General Formulas I, II, III, and IV. For example, the one or more substituted oxazoline compounds and/or substituted oxazoline derivatives in the ink composition may comprise a mixture of compounds wherein one or more of the compounds of General Formula IV is the major component of the phase-change agent.

In embodiments, the ink composition may comprise a colorant; a crystalline phase-change agent, and an amorphous binder agent or resin, wherein the ink includes one or more substituted oxazoline compounds and/or substituted oxazoline derivatives.

In embodiments, the substituted oxazoline compounds and/or substituted oxazoline derivatives that are suitable as crystalline phase change agents may be present in the ink in any desired amount, typically from about 20 to about 90 percent by weight, for example from about 40 to about 80 percent, or from about 50 to about 75 percent by weight of the total ink composition.

In embodiments, the amorphous substituted oxazoline compounds and/or substituted oxazoline derivatives may be present in the ink in any desired amount, typically from about 1 to about 75 percent, for example from about 5 to about 70 percent, from about 10 to about 60 percent by weight of the total ink composition.

In embodiments, the phase-change ink may optionally be a non-wax based solid ink that does not contain any major component comprised of wax-based compounds, wherein the major component is greater than 10 weight percent of the total ink composition.

In embodiments, the amorphous binder agent or resin of the ink composition comprises a dimer-oxazoline compound or dimer-oxazoline derivative.

In embodiments, an ink composition comprises one or more mono-oxazoline compounds having the general structure of Formula IV which may be either aromatic or aliphatic mono-oxazoline and which may optionally be in the form of an ester, such as aromatic esters or diesters and/or aliphatic esters) in any desired amount, such as in an amount of from about 0.5% to about 100%, or from about 2% to about 95%, or from about 5% to about 90% by weight of the ink composition.

In embodiments, the ink composition may be a solid at from about room temperature to about 60° C.

In embodiments, the one or more substituted oxazoline compounds and/or substituted oxazoline derivatives may be a mixture of compounds, where each oxazoline compound or oxazoline derivative may be a compound of General Formula IV. In embodiments, a specific component (such as phase-change agent, binder resin, compatibilizing agent, synergist, rheology modifier or plasticizer component) of an ink composition may include a substituted oxazoline compound or derivative having the general structure of General Formula IV in any desired amount, such as from about 1% to about 100%, or from about 2% to about 95%, or from about 5% to about 90% by weight of the total weight of the respective component (e.g., phase-change agent, binder resin, rheology modifier or plasticizer).

The compositions of embodiments, which may be incorporated into ink(s) or coatings, may further include conventional additives to take advantage of the known functionality associated with such additives. Such optional additives may include, for example, an antioxidant, defoamer, UV absorber, slip and leveling agents, synergists, adjuvants, clarifier, tackifier, adhesive, plasticizer and the like.

In embodiments, the ink may optionally contain antioxidants to protect the images from oxidation and also may protect the ink components from oxidation while existing as a heated melt in the ink reservoir. Examples of suitable antioxidants include (1) N,N'-hexamethylene bis(3,5-di-tert-butyl-4-hydroxy hydrocinnamamide) (IRGANOX 1098, available from Ciba Inc.), (2) 2,2-bis(4-(2-(3,5-di-tert-butyl-4-hydroxyhydrocinnamoyloxy))ethoxyphenyl) propane (TOPANOL-205, available from ICI America Corporation), (3) tris(4-tert-butyl-3-hydroxy-2,6-dimethyl benzyl) isocyanurate (CYANOX 1790, 41, 322-4, LTDP, Aldrich D12, 840-6), (4) 2,2'-ethylidene bis(4,6-di-tert-butylphenyl) fluoro phosphonite (ETHANOX-398, available from Ethyl Corporation), (5) tetrakis(2,4-di-tert-butylphenyl)-4,4'-biphenyl diphosphonite (ALDRICH 46, 852-5; hardness value 90), (6) pentaerythritol tetrastearate (TCI America #PO739), (7) tributylammonium hypophosphite (Aldrich 42, 009-3), (8) 2,6-di-tert-butyl-4-methoxyphenol (Aldrich 25, 106-2), (9) 2,4-di-tert-butyl-6-(4-methoxybenzyl)phenol (Aldrich 23, 008-1), (10) 4-bromo-2,6-dimethylphenol (Aldrich 34, 951-8), (11) 4-bromo-3,5-didimethylphenol (Aldrich B6, 420-2), (12) 4-bromo-2-nitrophenol (Aldrich 30, 987-7), (13) 4-(diethyl aminomethyl)-2,5-dimethylphenol (Aldrich 14, 668-4), (14) 3-dimethylaminophenol (Aldrich D14, 400-2), (15) 2-amino-4-tert-amylphenol (Aldrich 41, 258-9), (16) 2,6-bis (hydroxymethyl)-p-cresol (Aldrich 22, 752-8), (17) 2,2'-methylenediphenol (Aldrich B4, 680-8), (18) 5-(diethylamino)-2-nitrosophenol (Aldrich 26, 951-4), (19) 2,6-dichloro-4-fluorophenol (Aldrich 28, 435-1), (20) 2,6-dibromo fluoro phenol (Aldrich 26, 003-7), (21) α-trifluoro-o-creso-1 (Aldrich 21, 979-7), (22) 2-bromo-4-fluorophenol (Aldrich 30, 246-5), (23) 4-fluorophenol (Aldrich F1, 320-7), (24) 4-chlorophenyl-2-chloro-1,1,2-tri-fluoroethyl sulfone (Aldrich 13, 823-1), (25) 3,4-difluoro phenylacetic acid (Aldrich 29, 043-2), (26) 3-fluorophenylacetic acid (Aldrich 24, 804-5), (27) 3,5-difluoro phenylacetic acid (Aldrich 29, 044-0), (28) 2-fluorophenylacetic acid (Aldrich 20, 894-9), (29) 2,5-bis (trifluoromethyl)benzoic acid (Aldrich 32, 527-9), (30) ethyl-2-(4-(4-(trifluoromethyl)phenoxy)phenoxy) propionate (Aldrich 25, 074-0), (31) tetrakis(2,4-di-tert-butyl phenyl)-4,4'-biphenyl diphosphonite (Aldrich 46, 852-5), (32) 4-tert-amyl phenol (Aldrich 15, 384-2), (33) 3-(2H-benzotriazol-2-yl)-4-hydroxy phenethylalcohol (Aldrich 43, 071-4), NAUGARD 76, NAUGARD 445, NAUGARD 512, AND NAUGARD 524 (manufactured by Chemtura Corporation), and the like, as well as mixtures thereof. The antioxidant, when present, may be present in the ink in any desired or effective amount, such as from about 0.25 percent to about 10 percent by weight of the ink or from about 1 percent to about 5 percent by weight of the ink.

The ink may further contain an optional tackifier such as the commercial derivatives of rosin acids derived from gum rosins or tall oil resins. Representative examples include, but are not limited to, a glycerol ester of hydrogenated abietic (rosin) acid such as FORAL 85 (commercially available from Eastman), or a pentaerythritol ester of hydroabietic (rosin) acid such as FORAL 105 (commercially available from Eastman), or CELLOLYN 21, a hydroabietic (rosin) alcohol ester of phthalic acid (commercially available from Eastman), or triglycerides of hydrogenated abietic (rosin) acid such as KE-311 and KE-100 resins, (commercially available from Arakawa Chemical Industries, Ltd.), synthetic polyterpene resins such as NEVTAC 2300, NEVTAC 100, and NEVTACO 80 (commercially available from Neville Chemical Company), WINGTACK 86, a modified synthetic polyterpene resin (commercially available from Sartomer), and the like. Tackifiers may be present in the ink in any effective amount, such as from about 0.01 percent by weight of the ink to from about 30 percent by weight of the ink, from about 0.1 percent by weight of the ink to about 25 percent by weight of the ink, from about 1 weight percent of the ink to about 20 weight percent of the ink.

Plasticizers such as UNIPLEX 250 (commercially available from Unitex), the phthalate ester plasticizers commercially available from Ferro under the trade name SANTICIZER, such as dioctyl phthalate, diundecyl phthalate, alkylbenzyl phthalate (SANTICIZER 278), triphenyl phosphate (commercially available from Ferro), KP-140, a tributoxyethyl phosphate (commercially available from Great Lakes Chemical Corporation), MORFLEX 150, a dicyclohexyl phthalate (commercially available from Morflex Chemical Company Inc.), trioctyl trimellitate (commercially available from Sigma Aldrich Co.), and the like. Plasticizers may be present in an amount from about 0.01 to about 30 percent, from about 0.1 to about 25 percent, from about 1 to about 20 percent by weight of the ink.

In embodiments, the ink compositions described herein also includes at least one colorant. Any desired or effective colorant can be employed in the ink compositions, including dyes, pigments, mixtures thereof, and the like, provided that the colorant can be dissolved or dispersed in the ink carrier. Any dye or pigment may be chosen, provided that it is capable of being dispersed or dissolved in the ink carrier and is compatible with the other ink components. The ink compositions can be used in combination with conventional ink colorant materials, such as Color Index (C.I.) Solvent Dyes, Disperse Dyes, modified Acid and Direct Dyes, Basic Dyes, Sulphur Dyes, Vat Dyes, and the like. Examples of suitable dyes include Neozapon Red 492 (BASF); Orasol Red G (Ciba); Direct Brilliant Pink B (Oriental Giant Dyes); Direct Red 3BL (Classic Dyestuffs); Supranol Brilliant Red 3BW (Bayer AG); Lemon Yellow 6G (United Chemie); Light Fast Yellow 3G (Shaanxi); Aizen Spilon Yellow C-GNH (Hodogaya Chemical); Bernachrome Yellow GD Sub (Classic Dyestuffs); Cartasol Brilliant Yellow 4GF (Clariant); Cibanon Yellow 2GN (Ciba); Orasol Black CN (Ciba); Savinyl Black RLSN (Clariant); Pyrazol Black BG (Clariant); Morfast Black 101 (Rohm & Haas); Diaazol Black RN (ICI); Orasol Blue GN (Ciba); Savinyl Blue GLS (Clariant); Luxol Fast Blue MBSN (Pylam Products); Sevron Blue 5GMF (Classic Dyestuffs); Basacid Blue 750 (BASF), Neozapon Black X51 (BASF), Classic Solvent Black 7 (Classic Dyestuffs), Sudan Blue 670 (C.I. 61554) (BASF), Sudan Yellow 146 (C.I. 12700) (BASF), Sudan Red 462 (C.I. 26050) (BASF), C.I. Disperse Yellow 238, Neptune Red Base NB543 (BASF, C.I. Solvent Red 49), Neopen Blue FF-4012 from BASF, Lampronol Black BR from ICI (C.I. Solvent Black 35), Morton Morplas Magenta 36 (C.I. Solvent Red 172), metal phthalocyanine colorants such as those disclosed in U.S. Pat. No. 6,221,137, the disclosure of which is totally incorporated herein by reference, and the like. Other suitable dyes include those disclosed in U.S. Patent Application Publication No. 2010/0086683 and U.S. Pat. Nos. 7,732,581; 7,381,831; 6,713,614; 6,646,111; 6,590,082; 6,472,523; 6,713,614; 6,958,406; 6,998,493; 7,211,131; and 7,294,730, each of which is incorporated herein by reference in its entirety. Polymeric dyes can also be used, such as those disclosed in, for example, U.S. Pat. No. 5,621,022 and U.S. Pat. No. 5,231,135, the disclosures of each of which are herein entirely incorporated herein by reference, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactant Orange X-38, uncut Reactant Blue X-17, Solvent Yellow 162, Acid Red 52, Solvent Blue 44, and uncut Reactant Violet X-80.

In embodiments, solvent dyes are employed. Examples of suitable solvent dyes include Neozapon Red 492 (BASF); Orasol Red G (Ciba); Direct Brilliant Pink B (Global Colors); Aizen Spilon Red C-BH (Hodogaya Chemical); Kayanol Red 3BL (Nippon Kayaku); Spirit Fast Yellow 3G; Aizen Spilon Yellow C-GNH Chemical); Cartasol Brilliant Yellow 4GF (Clariant); Pergasol Yellow CGP (Ciba); Orasol Black RLP (Ciba); Savinyl Black RLS (Clariant); Morfast Black Conc. A (Rohm and Haas); Orasol Blue GN (Ciba); Savinyl Blue GLS (Sandoz); Luxol Fast Blue MBSN (Pylam); Sevron Blue 5GMF (Classic Dyestuffs); Basacid Blue 750 (BASF), Neozapon Black X51 [C.I. Solvent Black, C.I. 12195] (BASF), Sudan Blue 670 [C.I. 61554] (BASF), Sudan Yellow 146 [C.I. 12700] (BASF), Sudan Red 462 [C.I. 260501] (BASF), mixtures thereof and the like.

Pigments are also suitable colorants for the ink composition described herein. Examples of suitable pigments include PALIOGEN Violet 5100 (commercially available from BASF); PALIOGEN Violet 5890 (commercially available from BASF); HELIOGEN Green L8730 (commercially available from BASF); LITHOL Scarlet D3700 (commercially available from BASF); SUNFAST Blue 15:4 (commercially available from Sun Chemical); Hostaperm Blue B2G-D (commercially available from Clariant); Hostaperm Blue B4G (commercially available from Clariant); Permanent Red P-F7RK; Hostaperm Violet BL (commercially available from Clariant); LITHOL Scarlet 4440 (commercially available from BASF); Bon Red C (commercially available from Dominion Color Company); ORACET Pink RF (commercially available from Ciba); PALIOGEN Red 3871 K (commercially available from BASF); SUNFAST Blue 15:3 (commercially available from Sun Chemical); PALIOGEN Red 3340 (commercially available from BASF); SUNFAST Carbazole Violet 23 (commercially available from Sun Chemical); LITHOL Fast Scarlet L4300 (commercially available from BASF); SUNBRITE Yellow 17 (commercially available from Sun Chemical); HELIOGEN Blue L6900, L7020 (commercially available from BASF); SUNBRITE Yellow 74 (commercially available from Sun Chemical); SPECTRA PAC C Orange 16 (commercially available from Sun Chemical); HELIOGEN Blue K6902, K6910 (commercially available from BASF); SUNFAST Magenta 122 (commercially available from Sun Chemical); HELIOGEN Blue D6840, D7080 (commercially available from BASF); Sudan Blue OS (commercially available from BASF); NEOPEN Blue FF4012 (commercially available from BASF); PV Fast Blue B2GO1 (commercially available from Clariant); IRGALITE Blue BCA (commercially available from Ciba); PALIOGEN Blue 6470 (commercially available from BASF); Sudan Orange G (commercially available from Aldrich), Sudan Orange 220 (commercially available from BASF); PALIOGEN Orange 3040 (BASF); PALIOGEN Yellow 152, 1560 (commercially available from BASF); LITHOL Fast Yellow 0991K (commercially available from BASF); PALIOTOL Yellow 1840 (commercially available from BASF); NOVOPERM Yellow FGL (commercially available from Clariant); Ink Jet Yellow 4G VP2532 (commercially available from Clariant); Toner Yellow HG (commercially available from Clariant); Lumogen Yellow D0790 (commercially available from BASF); Suco-Yellow L1250 (commercially available from BASF); Suco-Yellow D1355 (commercially available from BASF); Suco Fast Yellow D1355, D1351 (commercially available from BASF); HOSTAPERM Pink E 02 (commercially available from Clariant); Hansa Brilliant Yellow 5GX03 (commercially available from Clariant); Permanent Yellow GRL 02 (commercially available from Clariant); Permanent Rubine L6B 05 (commercially available from Clariant); FANAL Pink D4830 (commercially available from BASF); CINQUASIA Magenta (commercially available from DU PONT); PALIOGEN Black L0084 (commercially available from BASF); Pigment Black K801 (commercially available from BASF); and carbon blacks such as REGAL 330™ (commercially available from Cabot), Nipex 150 (commercially available from Degusssa) Carbon Black 5250 and Carbon Black 5750 (commercially available from Columbia Chemical), and the like, as well as mixtures thereof. Other suitable pigments include those disclosed in U.S. Pat. Nos. 7,905,954; 7,503,973; 7,465,348; and 7,427,323.

The ink may also contain one or more dispersants and/or one or more surfactants for their known properties, such as for controlling wetting properties of the pigments in the ink composition. Examples of suitable additives that may be used in embodiments include, but are not limited to, BYK-UV 3500, BYK-UV 3510 (BYK-Chemie); Dow Corning 18, 27, 57, 67 Additives; ZONYL FSO 100 (DuPont); MODAFLOW 2100 (Solutia); Foam Blast 20F, 30, 550 (Lubrizol); EFKA-1101, -4046, -4047, -2025, -2035, -2040, -2021, -3600, -3232; SOLSPERSE 13000, 13240, 17000, 19200, 20000, 34750, 36000, 39000, 41000, 54000, individual dispersants or combinations may optionally be used with synergists including SOLSPERSE 5000, 12000, 22000 (Lubrizol); DISPERBYK-108, -163, -167, 182 (BYK-Chemie); K-SPERSE 132, XD-A503, XD-A505 (King Industries).

When present, the optional additives may each, or in combination, be present in the ink in any desired or effective amount, such as from about 0.1 to about 15 percent or from about 0.5 to about 12 percent by weight of the ink.

The amount of colorant in the phase-change ink of the present disclosure, may be from about 0.5% to about 20% or from about 1% to about 15% by weight, or from about 2% to about 10% by weight of the ink composition.

The ink compositions can be prepared by any desired or suitable method. For example, each of the components of the ink carrier can be mixed together, followed by heating, the mixture to at least its melting point, for example from about 60 to about 150° C., such as from about 80 to about 140° C., or from about 85 to about 120° C. The colorant may be added before the ink ingredients have been heated or after the ink ingredients have been heated. The molten mixture may optionally be subjected to grinding in an attritor, ball mill ore media mill apparatus, or to high shear mixing, in order to effect dispersion of the colorant in the ink carrier. The heated mixture is then stirred to obtain a uniform molten ink, followed by cooling the ink to ambient temperature (typically from about 20° C. to about 25° C.). The inks are solid at ambient temperature.

The inks can be employed in an apparatus for ink jet printing processes either directly to paper, or indirectly to an intermediate transfer member. Examples of apparatuses that are suitable for printing the phase-change inks described herein include apparatuses comprised of at least one thermally controlled ink retaining reservoir to store or hold molten phase-change ink, an ink jet head for printing the ink, and an ink supply line for providing the phase-change ink to the ink jet head.

Another embodiment disclosed herein is directed to a process which comprises incorporating an ink as disclosed herein into an ink jet printing apparatus, melting the ink, and causing droplets of the melted ink to be ejected in an imagewise pattern onto a recording substrate. Known direct printing process may be suitable for applying the ink compositions of the present disclosure onto a substrate.

Yet another embodiment disclosed herein is directed to a process which comprises incorporating an ink as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. In a specific embodiment, the intermediate transfer member is heated to a temperature above that of the final recording sheet and below that of the melted ink in the printing apparatus. In another specific embodiment, both the intermediate transfer member and the final recording sheet are heated; in this embodiment, both the intermediate transfer member and the final recording sheet are heated to a temperature below that of the melted ink in the printing apparatus; in this embodiment, the relative temperatures of the intermediate transfer member and the final recording sheet can be (1) the intermediate transfer member is heated to a temperature above that of the final recording substrate and below that of the melted ink in the printing apparatus; (2) the final recording substrate is heated to a temperature above that of the intermediate transfer member and below that of the melted ink in the printing apparatus; or (3) the intermediate transfer member and the final recording sheet are heated to approximately the same temperature. An offset or indirect printing process is also disclosed in, for example, U.S. Pat. No. 5,389,958, the disclosure of which is incorporated herein by reference. In one specific embodiment, the printing apparatus employs a piezoelectric printing process wherein droplets of the ink are caused to be ejected in imagewise pattern by oscillations of piezoelectric vibrating elements. Inks as disclosed herein can also be employed in other hot melt printing processes, such as hot melt acoustic ink jet printing, hot melt thermal ink jet printing, hot melt continuous stream or deflection ink jet printing, and the like. Phase-change inks as disclosed herein can also be used in printing processes other than hot melt ink jet printing processes, such as hot-melt lithographic, flexographic, and related offset ink printing processes.

Any suitable substrate or recording sheet can be employed such as plain paper, coated paper stocks and heavy paper stocks, transparency materials, fabrics, textile products, plastics, flexible polymeric films, inorganic substrates such as metals or silicon wafers, wood, and the like.

The inks described herein are further illustrated in the following examples. All parts and percentages are by weight unless otherwise indicated.

EXAMPLES

Example 1

Preparation of Dimer Oxazoline Compound 1 of Table 2 (n=10, $R_2$=$R_3$=H)

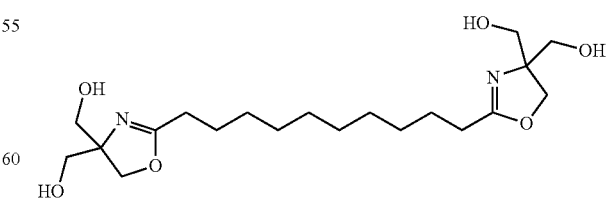

Into a 1 Liter Parr reactor equipped with a double turbine agitator, and distillation apparatus, was charged (in order): 1,12-dodecanedioic acid (291 g; SIGMA-ALDRICH Ltd., Milwaukee, Wis.), tris-(hydroxymethyl)aminomethane (306.9 g; EMD chemicals, New Jersey), and FASCAT 4100 catalyst (1.0 g, Arkema Inc.). The reaction mixture was heated to internal temperature of 165° C. for a 2 hour period, followed by increasing the temperature to 205° C. over another 2 hour period, during which time the water distillate was collected in a receiver. The reaction pressure was then reduced to approximately 1-2 mmHg for 1 hr, after which the contents were discharged into a tared container and cooled.

The crude product yield was approximately 480 g of a very hard, amber colored glass resin (estimated as 80% pure by $^1$H-NMR). The product was purified by first dissolving the crude compound in boiling methanol, which was then filtered hot to remove insoluble material, and then cool gradually to room temperature to afford the recrystallized product. After vacuum filtration and rinsing with cold methanol, the pure product is obtained as white granular powder, with peak melting point>170° C. (by DSC).

Example 2

Preparation of Amorphous Resin Mixture of Oxazoline Derivatives (Mixture Comprising Mono-Oxazoline Compounds 9-11 of Table 1, and Dimer Oxazoline Compound 3 of Table 2 where n=10 and $R_y$=OCH$_3$)

In 1 L stainless steel jacketed Buchi reactor equipped with distillation condenser, 4-blade impeller, and thermocouple was charged (in order): Dimer Oxazoline of Example 1 (30.04 g, 0.075 mol), 4-methoxybenzoic acid (228.2 g, 1.50 mol; SIGMA-ALDRICH, Milwaukee, Wis.), tris-(hydroxymethyl)aminomethane (51.48 g, 0.425 mol; obtained from EMD chemicals, New Jersey, 98%), and FASCAT 4100 as catalyst (0.26 g, 1.2 mmol; Arkema Inc.).

The mixture was heated up to about 160° C. external temperature under pressurized nitrogen atmosphere of 50 kPa without stirring. Once at this temperature, the stirring was started and the temperature raised gradually to 180° C. over 30 min, and then maintained for about 2 hrs. Water distillate from the condensation reaction was collected over this time period. The temperature was then increased to 190° C. and maintained for 1 hr, which produced more water distillate. Vacuum reduced pressure of 10 ton (approximately 10 mmHg) was applied for another 1 hr, which produced more water distillate. The reaction was thereafter stopped by cooling down to approximately 130° C., and then discharged into a tared container and cooled to room temperature.

The crude light amber-colored resin was obtained (400 grams) and used without further purification. The rheological analysis of this material was measured over a temperature range of 130° C. down to 40° C. using a RFS3 Rheometrics instrument (oscillation frequency of 1 Hz, 25 mm parallel

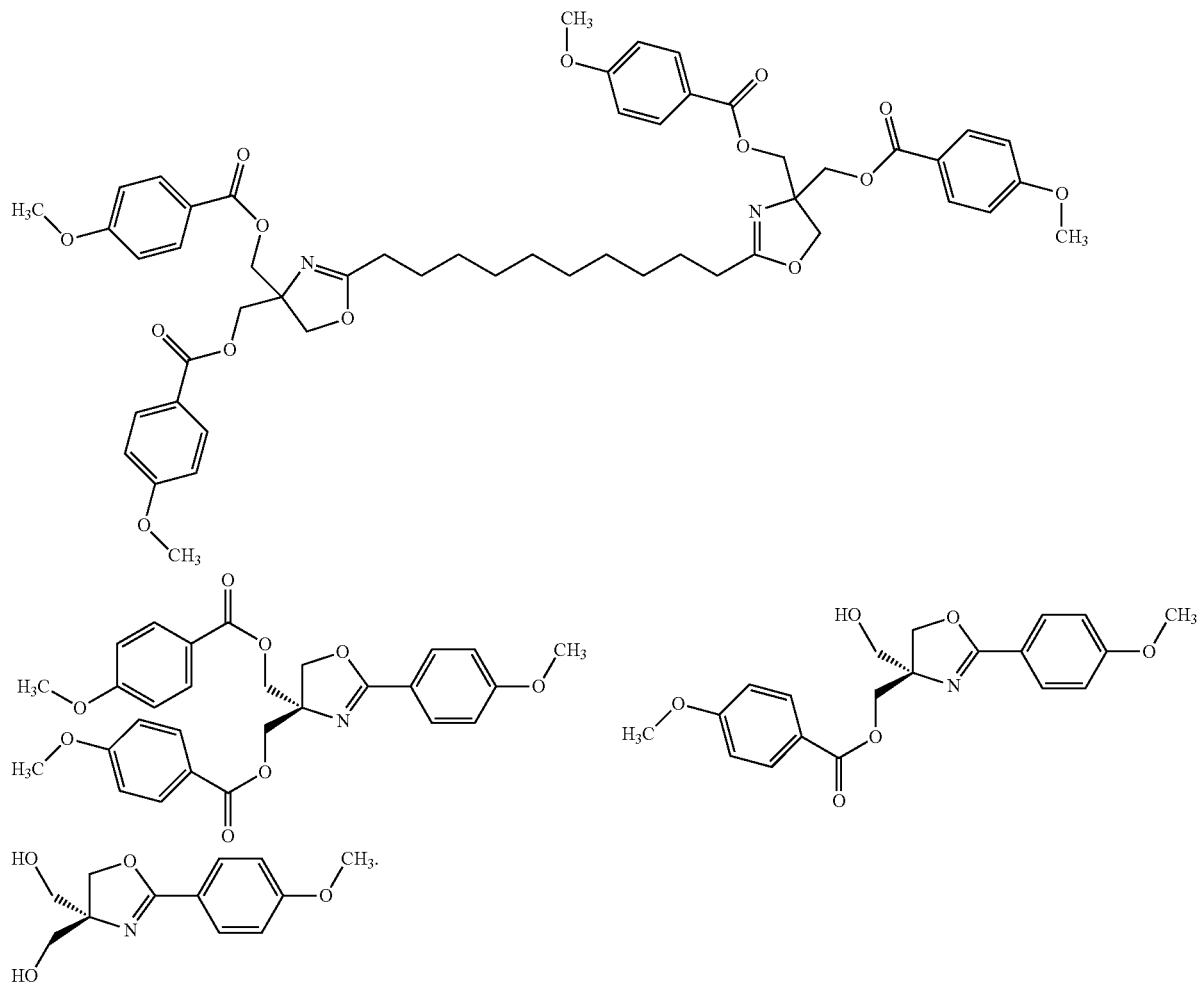

plate geometry, 200 applied strain %), and clearly displayed amorphous behavior (FIG. 2). The melt viscosity of this material at 130° C. was 75 cPs which increased to approximately $1.6 \times 10^5$ cPs at about 50° C.

Further, this compound exhibited suitable viscosity characteristics for use as an amorphous binder resin in a solid ink composition.

Example 3

Synthesis of Mono-Oxazoline Compound 5 of Table 1

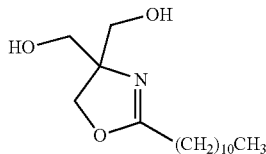

To a 1 Liter Pan reactor equipped with a double turbine agitator, and distillation apparatus, was charged with dodecanoic acid (200 grams; SIGMA-ALDRICH, Milwaukee, Wis.), of tris(hydroxymethyl)aminomethane (92 grams; EMD Chemicals, New Jersey), and FASCAT 4100 as catalyst (0.45 grams; Arkema Inc). The contents were heated to 165° C. for a 2 hour period, followed by increasing the temperature to 205° C. over a 2 hour period during which time the water distillate was collected in a distillation receiver. The reactor pressure was then reduced to about 1-2 mm-Hg for one hour, followed by discharging into a tared container and cooled to room temperature. The product was purified by dissolving with mild heating in a mixture of ethyl acetate (2.5 parts) and hexane (10 parts), and then cooling to room temperature to crystallize the pure product as a white granular powder. The peak melting point (DSC) was determined to be 99° C.

The rheological analysis of this material was measured over a temperature range of 130° C. down to 40° C. using a RFS3 Rheometrics instrument (oscillation frequency of 1 Hz, 25 mm parallel plate geometry, 200 applied strain %). Shown in FIG. 2 is a plot of complex viscosity versus temperature, which showed that melt viscosity at 130° C. was 8.2 cPs, and the onset of crystallization of this material occurred at 95° C., with a peak viscosity of $4.5 \times 10^6$ cPs (at full crystallization temperature of 85° C.).

Example 4

Preparation of Dimer Oxazoline Ester (Compound 7, Table 2 where group $R_1$ has n=11 and group $R_2$ has n=10)

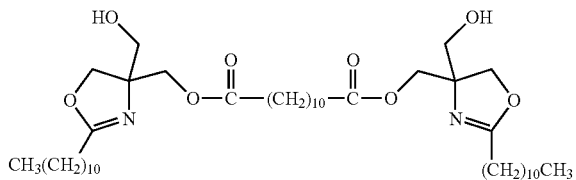

In a 100 mL, three-necked round bottom flask equipped with short-path distillation apparatus and temperature probe, was charged: mono-oxazoline diol of Example 4 (3.425 g), 1,12-dodecanedioic acid (1.38 grams; SIGMA-ALDRICH, Milwaukee, Wis.), and FASCAT 4100 as catalyst (6.3 mg; Arkema Inc). The contents were gradually heated to 165° C. over a 1 hour period while being stirred magnetically at 400 rpm. Once water vapor was observed to evolve, the mixture was heated at 165° C. for another 2 hr period, after which time all of the mono-oxazoline diol was consumed (as monitored by $^1$H-NMR spectroscopy). The reactor pressure was then reduced to about 10 mm-Hg for about 2 min, followed by discharging into a tared container and cooled to room temperature. The product was not purified further, and was isolated as an opaque, pale yellow semi-solid (3.60 g). The DSC thermal analysis of this material measured at a heating rate of 10° C./min showed only one crystalline melt transition at 8.6° C. and a glass transition (Tg) onset temperature at approximately 41° C.

The rheological analysis of this material was measured over a temperature range of 130° C. down to 40° C. using a RFS3 Rheometrics instrument (oscillation frequency of 1 Hz, 25 mm parallel plate geometry, 200 applied strain %), which displayed clearly amorphous behavior. The melt viscosity of this material at 130° C. was 27.5 cPs which increased to approximately $2 \times 10^3$ cPs at about 40° C.

Example 5

Preparation of Dimer Oxazoline Ester (Compound 17, Table 2 where group $R_1$ has n=11)

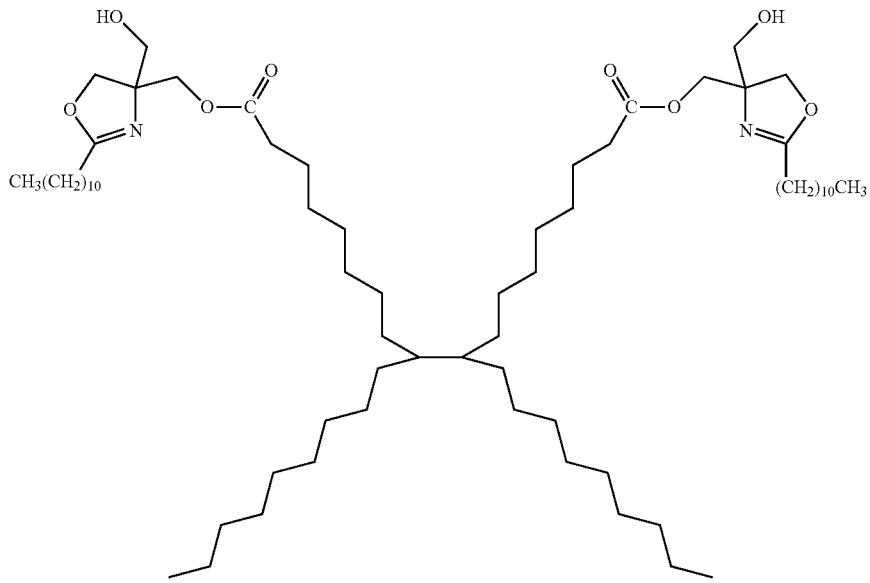

In a 100 mL, three-necked round bottom flask equipped with short-path distillation apparatus and temperature probe, was charged: mono-oxazoline diol of Example 4 (1.38 g), C-36 "Dimer Acid" (5.10 grams; commercially sold as Pripol 1006 from Uniqema Inc., Delaware, USA), and FASCAT 4100 as catalyst (2.5 mg; Arkema Inc). The contents were gradually heated to 165° C. over a 1 hour period while being stirred magnetically at 400 rpm. Once water vapor was observed to evolve, the mixture was heated at 165° C. for another 2.5 hr period, after which time all of the mono-oxazoline diol was consumed (as monitored by $^1$H-NMR spectroscopy). The reactor pressure was then reduced to about 10 mm-Hg for about 2 min, followed by discharging into a tared container and cooled to room temperature. The product was not purified further, and was isolated as a clear, pale yellow semi-solid (5.35 g). The DSC thermal analysis of this material measured at a heating rate of 10° C./min did not showed any crystalline thermal transitions nor any well-defined glass transitions (Tg).

The rheological analysis of this material was measured over a temperature range of 130° C. down to 40° C. using a RFS3 Rheometrics instrument (oscillation frequency of 1 Hz, 25 mm parallel plate geometry, 200 applied strain %), which displayed clearly amorphous behavior. The melt viscosity of this material at 130° C. was 113 cPs which increased to approximately $1.3 \times 10^4$ cPs at about 40° C.

Examples 6 to 8

Preparation of Phase Change Ink Compositions, According to Table 3

As shown Table 3 (below), phase change ink compositions were formulated using mixtures of the oxazoline compounds described herein.

A general procedure for preparation of a solid ink composition (scale of 50 grams or higher) was as follows:
Into a 250 mL glass or stainless steel vessel was charged, in the following order:
 i) Amorphous binder resin material;
 ii) Crystalline phase change material;
 iii) Additives (viscosity modifiers, anti-oxidants, tackifiers, clarifiers, etc.).

The mixture was first melted at high temperatures, such as 120° C. or higher, and then placed into a temperature controlled heating mantle where it was melt mixed at 130° C. using a mechanical overhead stirrer equipped with stainless steel 4-blade 90° pitch impeller stirring at approximately 175-250 rpm. This ink base mixture was stirred for at least 1 hr before subjecting it to heated filtration through a stainless steel 325×2300 mesh wire filter cloth (type 304 SS obtained from Gerard Daniel Worldwide, Hanover, USA). The filtered ink base was then transferred back to a 250 mL vessel and stirred mechanically while heating at 130° C. To this ink base was added the desired colorant in small portions over a 0.5 hr period of time while continuing to heat. Once the colorant addition was completed, the colored ink composition was allowed to stir for addition 3-4 hrs at 130° C. while stirring at 275 rpm, to ensure homogeneity of the ink composition. The colored ink composition was then filtered molten once more through the steel 325×2300 mesh wire filter cloth, before being dispensed into mould trays and solidified while cooling at room temperature. The colored ink compositions were characterized for thermal properties by DSC and for rheological properties using the Rheometrics RFS3 strain-controlled rheometer instrument.

Table 3 shows the various components of exemplary ink compositions. Rheological profiles of the ink compositions are shown FIG. 3.

TABLE 3

Phase Change Ink Compositions

| Component | | Example 5 Wt % | Example 6 Wt % | Example 7 Wt % |
|---|---|---|---|---|
| Crystalline Phase-change agent | Example 3 Material (a Mono-Oxazoline Diol) | 62.80 | 63.5 | 63.5 |
| Amorphous Binder Resin | Example 2 Oxazoline Material | 30.00 | 30.00 | 30.00 |
| Viscosity modifier | (KEMAMIDE S-180 (Stearyl stearamide, obtained from Witco Corp., USA) | 4.00 | 3.50 | 3.50 |
| Antioxidant | Naugard 445 (obtained from Chemtura, USA) | 0.20 | 0.00 | 0.00 |
| Colorant | Orasol Blue GN dye (obtained from Ciba-Geigy, USA) | 3.00 | 3.00 | 3.00 |
| Ink Properties | *Viscosity @ 130° C. (cPs) | 11.15 | 11.20 | 11.20 |
| | *Viscosity @ 60° C. (cPs) | $6.8 \times 10^6$ | $4.5 \times 10^6$ | $6 \times 10^7$ |
| | Onset Tcryst. (° C.) (by rheology) | 78 | 86 | 90 |
| | Melt Temp (° C.) (by DSC**) | 81.5 | 87 | 89 |
| | Tcryst. (° C.) (by DSC**) | 62 (small) 54 (large) | 63 | 66.5 |

*Oscillation Frequency = 1 Hz; 25 mm parallel plate geometry; gap = 0.2 mm; strain % = 200%-400%, strain independent viscosities as measured on a Rheometrics RFS3 instrument.
**DSC analysis performed on a TA Instruments Q1000 machine, measured after two heating and cooling cycles using a scan rate of 10° C./min.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A composition comprising:
one or more compounds represented by General Formula II

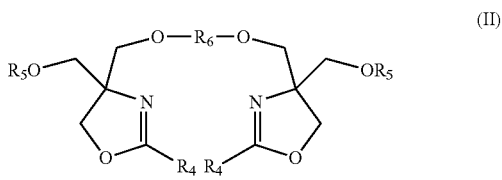

(II)

wherein
 $R_4$ is an alkyl group, aryl group, alkylaryl group, or an aromatic group;
 $R_5$ is an alkyl group, aryl group, alkylaryl group, aromatic group, a hydrogen, —(C=O)—(CH$_2$)$_s$CH$_3$ in which s is zero or an integer in a range from 1 to about 50,

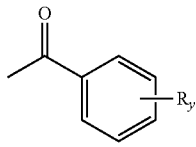

wherein $R_y$ is H, OH, $OCH_3$, Cl, Dr, F, I, $NH(COCH_3)$, $CH_3$, $CH_2CH_3$, isopropyl, t-butyl, $CO_2CH_3$, $CO_2H$, an alkyl group having from 1 to about 66 carbons, or alkoxy group having from 1 to about 8 carbons, or —(C=O)—NH—$R_z$, where $R_z$ is either a linear alkyl group of the formula —$(CH_2)_tCH_3$ wherein t is either zero or an integer of from 1 to about 36, or where $R_z$ is an alkylaryl group containing from about 6 to about 20 carbon atoms;

$R_6$ is an alkylene group, arylene group, arylalkylene group, alkylarylene group,

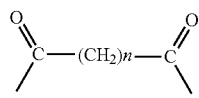

in which n is an integer in a range from about 6 to about 36,

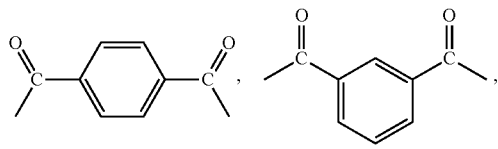

a branched alkylene group of general formula $C_{36}H_{64+u}$, wherein u is an integer in the range from 0 to about 10,

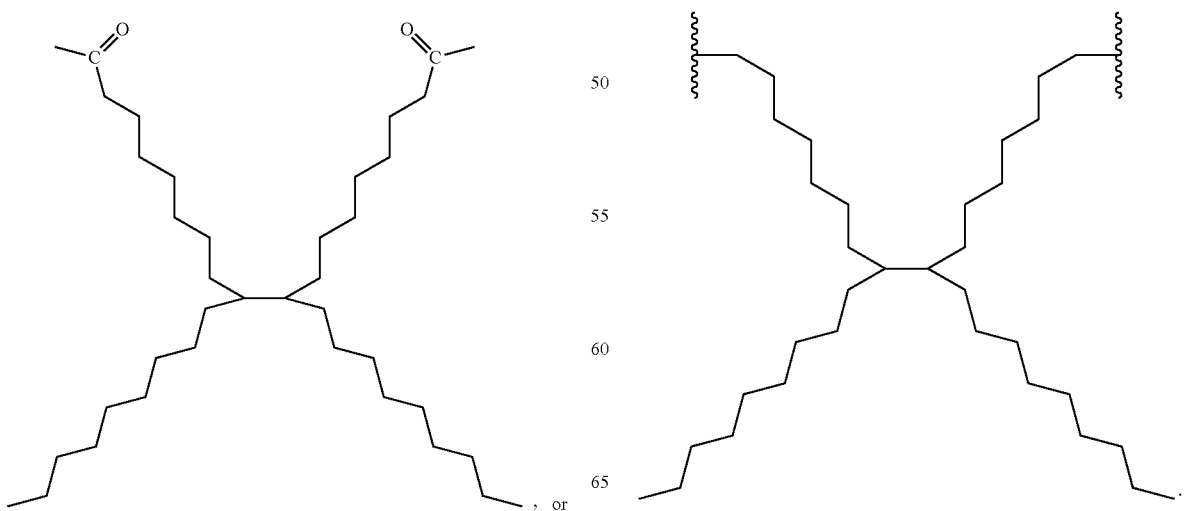
, or

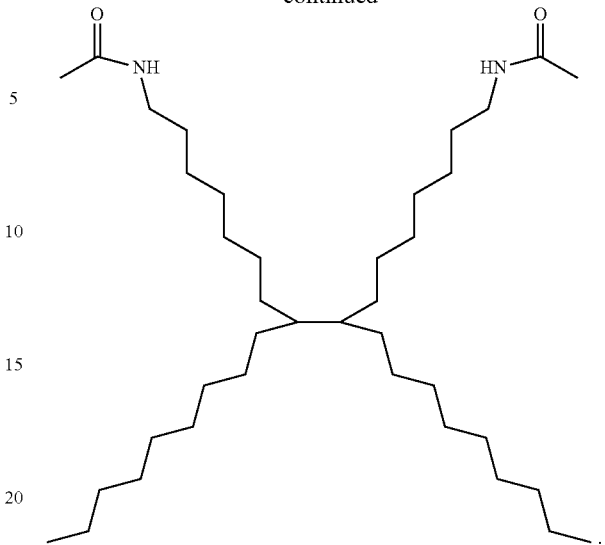

2. The composition of claim 1, wherein composition comprises one or more compounds represented by General Formula II in which $R_6$ is
a divalent aromatic or aryl group having about 5 to about 20 carbon atoms,

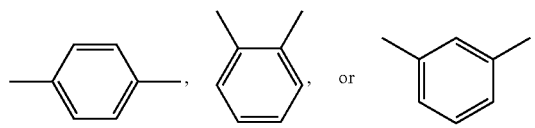

3. The composition of claim 1, wherein composition comprises one or more compounds represented by General Formula II in which $R_6$ is
a divalent aliphatic or alkyl group, including linear and branched, saturated and unsaturated, cyclic and acyclic, and substituted and unsubstituted divalent aliphatic or alkyl groups.

4. The composition of claim 1, wherein the alkylene group is a branched alkylene group of general formula $C_{36}H_{60+u}$, wherein u is an integer in the range from about 0 to about 14.

5. The composition of claim 4, wherein the alkylene group is

6. The composition of claim 1, wherein the composition comprises one or more compounds represented by General Formula II in which $R_5$ is

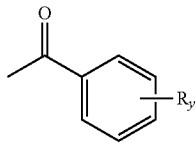

wherein $R_y$ is H, OH, $OCH_3$, Cl, Br, F, I, $NH(COCH_3)$, $CH_3$, $CH_2CH_3$, isopropyl, t-butyl, $CO_2CH_3$, $CO_2H$, an alkyl group having from 1 to about 66 carbons, or alkoxy group having from 1 to about 8 carbons.

7. The composition of claim 1, wherein the composition further comprises
one or more compounds represented by General Formula I'

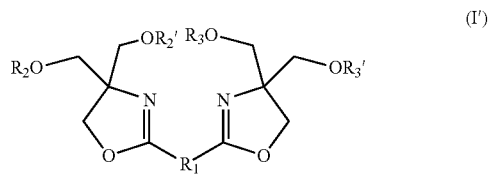

where $R_1$, $R_2$, $R_2'$, $R_3$ and $R_3'$ are defined as set forth in the following table:

| $R_1$ | $R_2$ ($R_2'$) | $R_3$ ($R_3'$) |
| --- | --- | --- |
| —$(CH_2)_w$— where w is 2, 4, 8, 10, 12, or 16 | H | H |
| —$(CH_2)_w$— where w is 2, 4, 8, 10, 12, or 16 | —(C=O)—$(CH_2)_s CH_3$ where s is 2, 4, 6, 10, 14, or an integer in the range of from about 30 to about 50 | —(C=O)—$(CH_2)_s CH_3$ where s is 2, 4, 6, 10, 14, or an integer in the range of from about 30 to about 50 |
| —$(CH_2)_w$— where w is 2, 4, 8, 10, 12, or 16 | where $R_y$ is H, OH, $OCH_3$, Cl, Br, F, I, $NH(COCH_3)$, $CH_3$, isopropyl, t-butyl, $CO_2CH_3$, $CO_2H$, $(CH_2)_{m'}CH_3$ where m' is an integer in the range of from 1 to about 17, or $O(CH_2)_p CH_3$ where p is an integer in the range of from 1 to about 7 | where $R_y$ is H, OH, $OCH_3$, Cl, Br, F, I, $NH(COCH_3)$, $CH_3$, isopropyl, t-butyl, $CO_2CH_3$, $CO_2H$, $(CH_2)_{m'}CH_3$ where m' is an integer in the range of from 1 to about 17, and $O(CH_2)_p CH_3$ where p is an integer in the range of from 1 to about 7 |
| $C_{36}H_{64+u}$ branched alkylene group, where u is an integer in the range from about 0 to about 10, including structural isomer | H | H |

-continued
| R₁ | R₂ (R₂') | R₃ (R₃') |
|---|---|---|
| 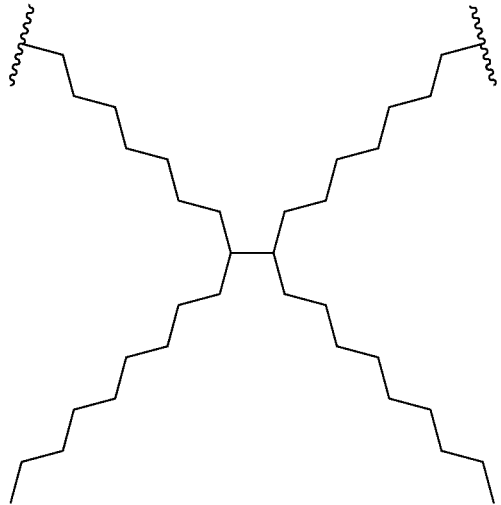 [SMILES: *CCCCCCCC(CCCCCCCCC)C(CCCCCCC*)CCCCCCCCC]<br><br>$C_{36}H_{64+u}$ branched alkylene group, where u is an integer in the range from about 0 to about 10, including structural isomer<br><br>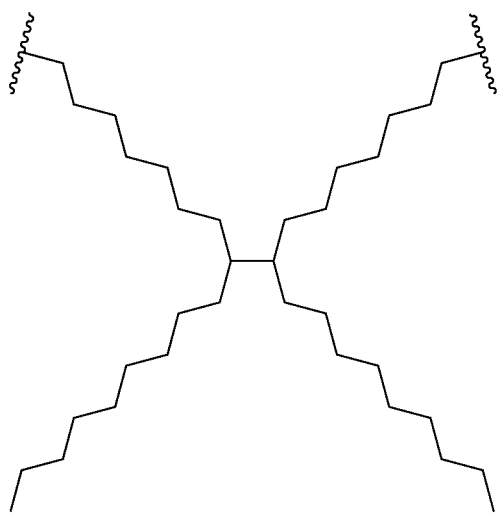 [SMILES: *CCCCCCCC(CCCCCCCCC)C(CCCCCCC*)CCCCCCCCC] | —(C=O)—(CH₂)ₛCH₃ where s = 2, 4, 6, 10, 14, or an integer in the range of from about 30 to about 50 | —(C=O)—(CH₂)ₛCH₃ where s = 2, 4, 6, 10, 14, or an integer in the range of from about 30 to about 50 |

-continued

| $R_1$ | $R_2$ ($R_2'$) | $R_3$ ($R_3'$) |
|---|---|---|
| $C_{36}H_{64+u}$ branched alkylene group, where u is an integer in the range from about 0 to about 10, including structural isomer 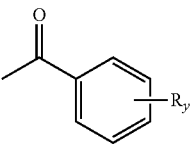 | 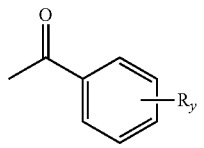 where $R_y$ is H, OH, $OCH_3$, Cl, Br, F, I, $NH(COCH_3)$, $CH_3$, isopropyl, t-butyl, $CO_2CH_3$, $CO_2H$, $(CH_2)_{m'}CH_3$ where m' is an integer in the range of from 1 to about 17, or $O(CH_2)_pCH_3$ where p is an integer in the range of from 1 to about 7 | 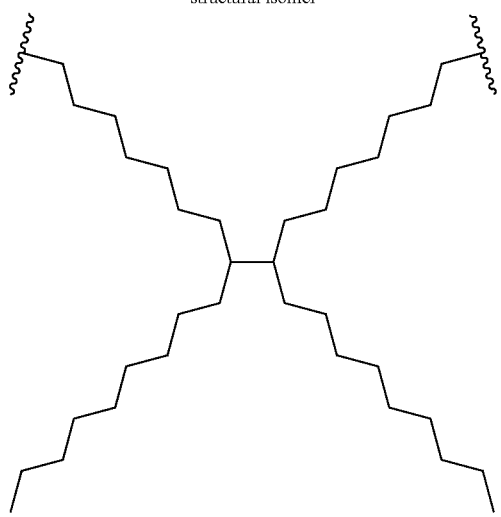 where $R_y$ is H, OH, $OCH_3$, Cl, Br, F, I, $NH(COCH_3)$, $CH_3$, isopropyl, t-butyl, $(CH_2)_{m'}CH_3$ where m' is an integer in the range of from 1 to about 17, or $O(CH_2)_pCH_3$ where p is an integer in the range of from 1 to about 7 |
| $-(CH_2)_w-$ where w is an integer in the range of from 1 to about 16 | $-(C{=}O)-NH(CH_2)_vCH_3$ where v is an integer in the range of from about 5 to about 17 | $-(C{=}O)-NH(CH_2)_vCH_3$ where v is an integer in the range of from about 5 to about 17 | wherein, the one or more compounds represented by General Formula II

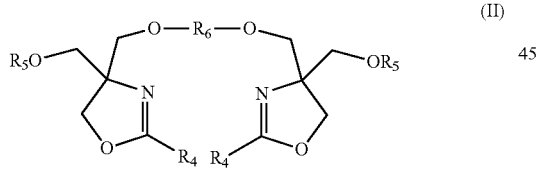

(II)

where each $R_4$ may be the same or different, each $R_5$ may be the same or different, and $R_4$, $R_5$ and $R_6$ are defined as set forth in the following table:

| $R_4$ | $R_6$ | $R_5$ |
|---|---|---|
| $-(CH_2)_tCH_3-$ where t is an integer in the range of from 1 to about 17 | 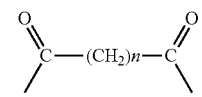 where n is an integer in the range of from 1 to about 16 | H |

-continued

| $R_4$ | $R_6$ | $R_5$ |
|---|---|---|
| —(CH$_2$)$_t$CH$_3$— where t is an integer in the range of from 1 to about 17 | 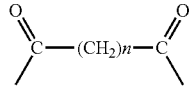 where n is an integer in the range of from 1 to about 16 | 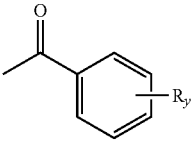 where $R_y$ is H, OH, OCH$_3$, Cl, Br, F, I, NH(COCH$_3$), CH$_3$, isopropyl, t-butyl, CO$_2$CH$_3$, CO$_2$H, (CH$_2$)$_{m'}$CH$_3$ where m' is an integer in the range of from 1 to about 17, or O(CH$_2$)$_p$CH$_3$ where p is an integer in the range of from 1 to about 7 |
| —(CH$_2$)$_t$CH$_3$— where t is an integer in the range of from 1 to about 17 | 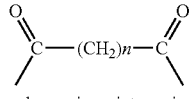 where n is an integer in the range of from 1 to about 16 | —(C═O)—(CH$_2$)$_s$CH$_3$ where s is 2, 4, 6, 10, 14, or an integer in the range of from about 30 to about 50 |
| 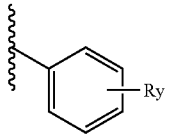 where $R_y$ is H, OH, OCH$_3$, Cl, Br, F, I, NH(COCH$_3$), CH$_3$, isopropyl, t-butyl, CO$_2$CH$_3$, CO$_2$H, or (CH$_2$)$_2$CH$_3$ | 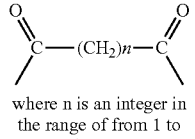 where n is an integer in the range of from 1 to about 16 | H |
| 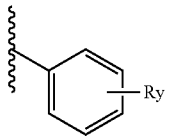 where $R_y$ is H, OH, OCH$_3$, Cl, Br, F, I, NH(COCH$_3$), CH$_3$, isopropyl, t-butyl, CO$_2$CH$_3$, CO$_2$H, or (CH$_2$)$_2$CH$_3$ | 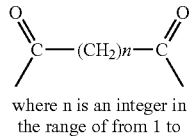 where n is an integer in the range of from 1 to about 16 | 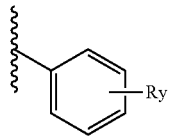 where $R_y$ is H, OH, OCH$_3$, Cl, Br, F, I, NH(COCH$_3$), CH$_3$, isopropyl, t-butyl, CO$_2$CH$_3$, CO$_2$H, or (CH$_2$)$_2$CH$_3$ |
| 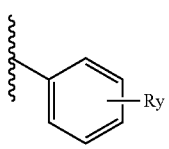 where $R_y$ is H, OH, OCH$_3$, Cl, Br, F, I, NH(COCH$_3$), CH$_3$, isopropyl, t-butyl, CO$_2$CH$_3$, CO$_2$H, or (CH$_2$)$_2$CH$_3$ | 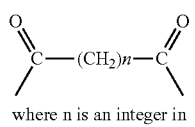 where n is an integer in the range of from 1 to about 16 | —(C═O)—(CH$_2$)$_s$CH$_3$ where s is 2, 4, 6, 10, 14, or an integer in the range of from about 30 to about 50 |

-continued

| $R_4$ | $R_6$ | $R_5$ |
|---|---|---|
| —$(CH_2)_tCH_3$— where t is an integer in the range of from 1 to about 17 | [structure: —C(=O)—C$_6$H$_4$—C(=O)— (para)] | H |
| —$(CH_2)_tCH_3$— where t is an integer in the range of from 1 to about 17 | [structure: —C(=O)—C$_6$H$_4$—C(=O)— (para)] | —(C=O)—$(CH_2)_sCH_3$ where s is 2, 4, 6, 10, 14, or an integer in the range of from about 30 to about 50 |
| —$(CH_2)_tCH_3$— where t is an integer in the range of from 1 to about 17 | [structure: —C(=O)—C$_6$H$_4$—C(=O)— (meta)] | H |
| —$(CH_2)_tCH_3$— where t is an integer in the range of from 1 to about 17 | [structure: —C(=O)—C$_6$H$_4$—C(=O)— (meta)] | —(C=O)—$(CH_2)_sCH_3$ where s is 2, 4, 6, 10, 14, or an integer in the range of from about 30 to about 50 |
| —$(CH_2)_tCH_3$— where t is an integer in the range of from 1 to about 17 | $C_{36}H_{64+u}$ branched alkylene group, where u is an integer in the range from about 0 to about 10, including structural isomer [branched alkylene structure shown] | H |
| —$(CH_2)_tCH_3$— where t is an integer in the range of from 1 to about 17 | $C_{36}H_{64+u}$ branched alkylene group, where u is an integer in the range from about 0 to about 10, including structural isomer | —(C=O)—$(CH_2)_sCH_3$ where s is 2, 4, 6, 10, 14, or an integer in the range of from about 30 to about 50 |

| $R_4$ | $R_6$ | $R_5$ |
|---|---|---|
| | 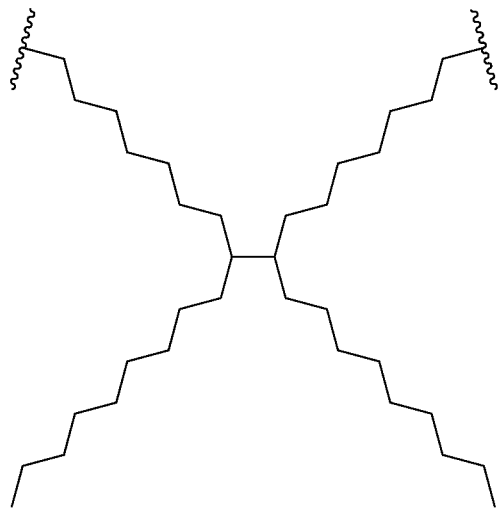 [SMILES: *CCCCCCCC(CCCCCCCCC)C(CCCCCCC*)CCCCCCCCC] | |
| —$(CH_2)_tCH_3$— where t is an integer in the range of from 1 to about 17 | 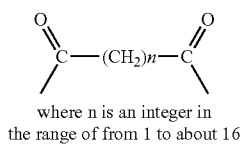 where n is an integer in the range of from 1 to about 16 | 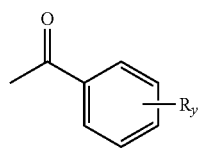 where $R_y$ is H, OH, OCH$_3$, Cl, Br, F, I, NH(COCH$_3$), CH$_3$, isopropyl, t-butyl, CO$_2$CH$_3$, CO$_2$H, $(CH_2)_{m'}CH_3$ where m' is an integer in the range of from 1 to about 17, or $O(CH_2)_pCH_3$ where p is an integer in the range of from 1 to about 7 |
| —$(CH_2)_tCH_3$— where t is an integer in the range of from 1 to about 17 | 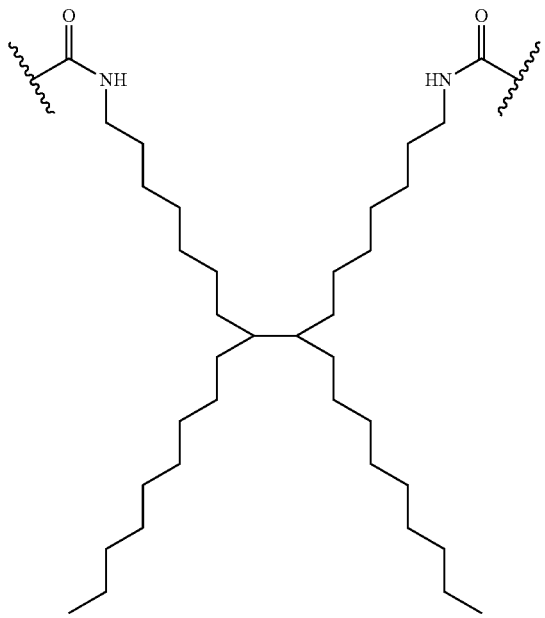 [SMILES: *C(=O)NCCCCCCCC(CCCCCCCCC)C(CCCCCCCCC)CCCCCCCNC(*)=O] | H. |

8. The composition of claim 1, wherein the composition further comprises one or more compounds selected from the group consisting of:

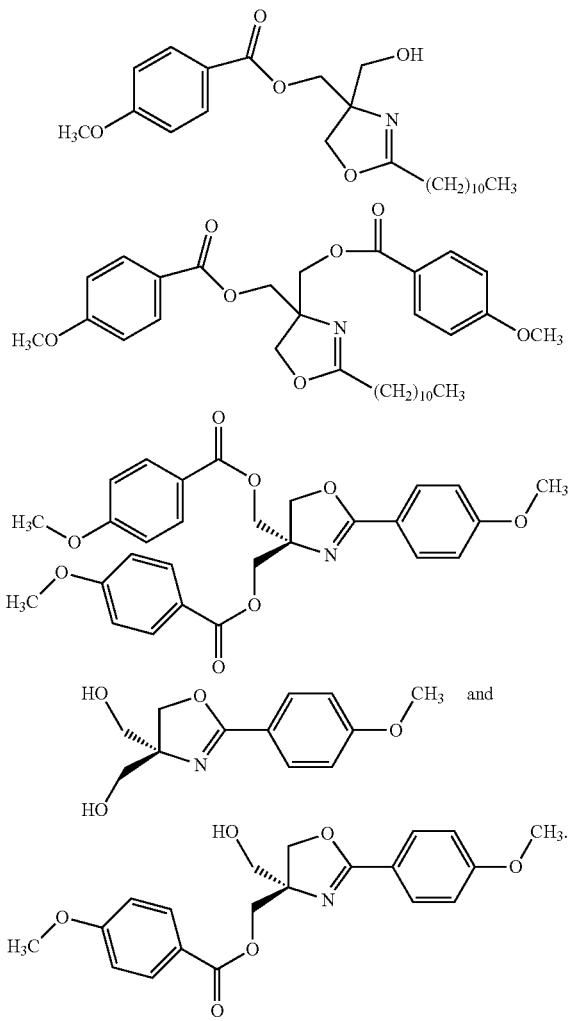

9. The composition of claim 1, wherein the composition further comprises:

one or more compounds represented by General Formula I

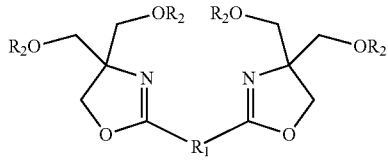

(I)

wherein

R$_1$ is an alkylene group, arylene group, arylalkylene group, alkylarylene group; and R$_2$ is an alkyl group, aryl group, alkylaryl group, aromatic group, a hydrogen, —(C=O)—(CH$_2$)$_s$CH$_3$ in which s is zero or an integer in a range from 1 to about 50,

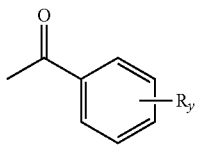

wherein R$_y$ is H, OH, OCH$_3$, Cl, Br, F, I, NH(COCH$_3$), CH$_3$, CH$_2$CH$_3$, isopropyl, t-butyl, CO$_2$CH$_3$, CO$_2$H, an alkyl group having from 1 to about 66 carbons, or alkoxy group having from 1 to about 8 carbons, or —(C=O)—NH—R$_t$, where R$_t$ is either a linear alkyl group of the formula —(CH$_2$)$_t$CH$_3$ wherein t is either zero or an integer of from 1 to about 36, or where R$_t$ is an alkylaryl group containing from about 6 to about 20 carbon atoms;

one or more compounds represented by general Formula III

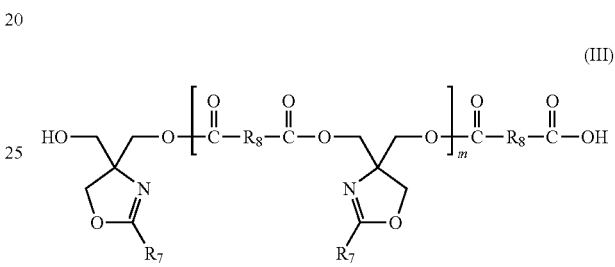

(III)

in which m is an integer of from 1 to about 100, wherein

R$_7$ is an alkyl group, aryl group, alkylaryl group, or an aromatic group; and

R$_8$ is an alkylene group, arylene group, arylalkylene group, alkylarylene group,

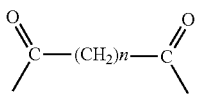

in which n is an integer in a range from about 6 to about 36, a branched alkylene group of general formula C$_{34}$H$_{60+u}$, wherein u is an integer in the range from about 0 to about 14,

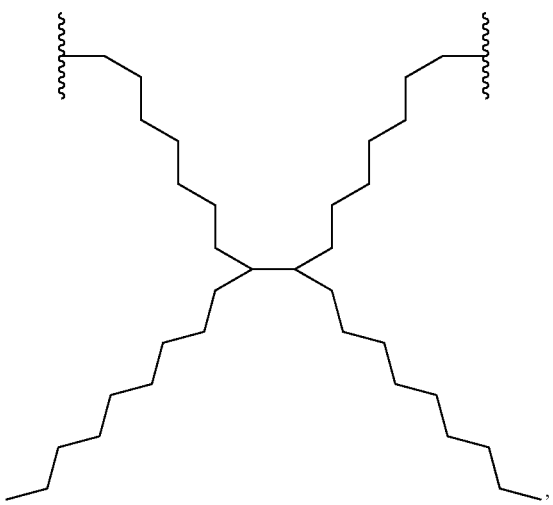

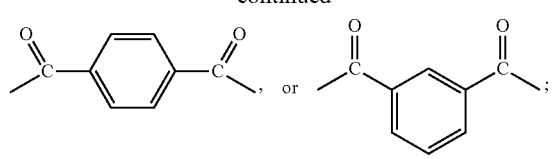

one or more compounds represented by general Formula IV

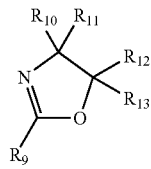

(IV)

wherein

R$_9$ is an alkyl group, aryl group, alkylaryl group, or aromatic group;

R$_{10}$, R$_{11}$, R$_{12}$ and R$_{13}$ are the same or different and are an alkyl group, aryl group, alkylaryl group, alkoxy group, or aromatic group, an hydroxyalkyl of form about 1 to about 60 carbons, an alkyl ester of from about 1 to about 60 carbons, or an aryl ester, wherein at least one of R$_9$, R$_{10}$, R$_{11}$, R$_{12}$ and R$_{13}$ is an aromatic group.

10. The composition of claim 1, wherein composition comprises one or more compounds represented by General Formula II in which R$_6$ is selected from the group consisting of a branched alkylene group of general formula C$_{36}$H$_{64+u}$, wherein u is an integer in the range of from about 0 to about 10,

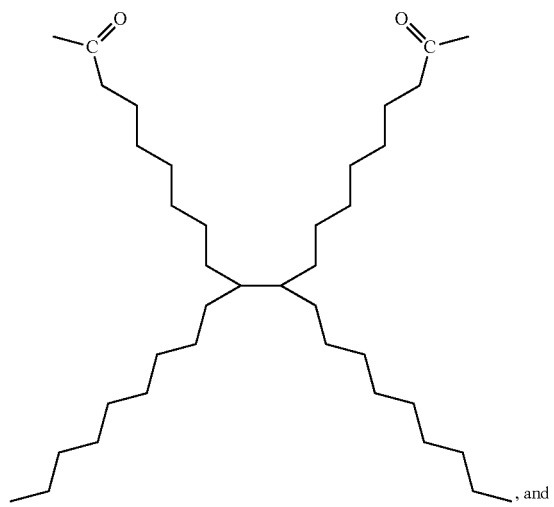

, and

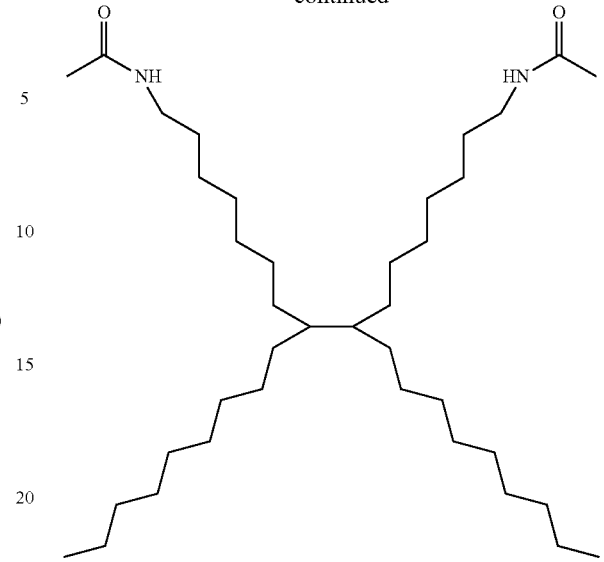

11. The composition of claim 1, wherein the composition of claim 1 makes up, entirely or in part, one or more components of an ink composition, wherein the one or more components are selected from the group consisting of crystalline phase-change agents, binder resins, compatibilizing agents, synergists, rheology modifiers, tackifiers and plasticizers.

12. The composition of claim 1, wherein the melting temperature of the composition is from about 60° C. to about 130° C., or the crystallization temperature is from about 50° C. to about 120° C.

13. A method of producing compounds of General Formula II

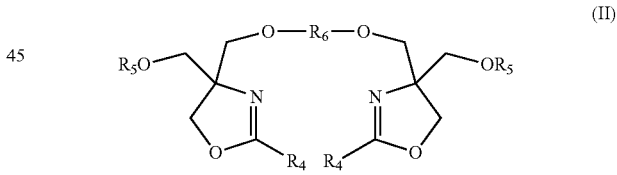

(II)

wherein

R$_4$ is an alkyl group, aryl group, alkylaryl group, or an aromatic group;

R$_6$ is an alkyl group, aryl group, alkylaryl group, aromatic group, a hydrogen, —(C=O)—(CH$_2$)$_s$CH$_3$ in which s is zero or an integer in a range from 1 to about 50,

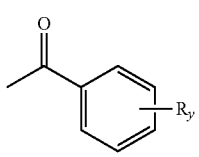

wherein $R_y$ is H, OH, $OCH_3$, Cl, Br, F, I, $NH(COCH_3)$, $CH_3$, $CH_2CH_3$, isopropyl, t-butyl, $CO_2CH_3$, $CO_2H$, an alkyl group having from 1 to about 66 carbons, or alkoxy group having from 1 to about 8 carbons, or —(C=O)—NH—$R_z$, where $R_z$ is either a linear alkyl group of the formula —$(CH_2)_t CH_3$ wherein t is either zero or an integer of from 1 to about 36, or where $R_z$ is an alkylaryl group containing from about 6 to about 20 carbon atoms;

$R_6$ is an alkylene group, arylene group, arylalkylene group, alkylarylene group,

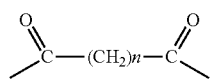

in which n is an integer in a range from about 6 to about 36,

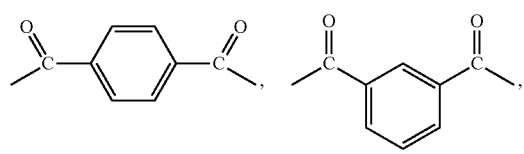

a branched alkylene group of general formula $C_{36}H_{64+u}$, wherein u is an integer in the range from 0 to about 10,

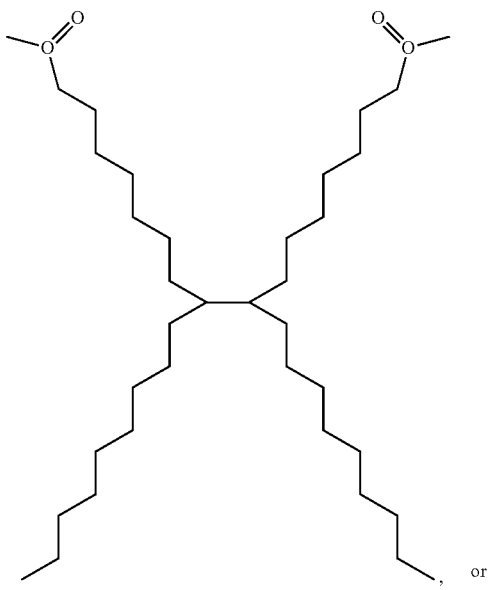

, or

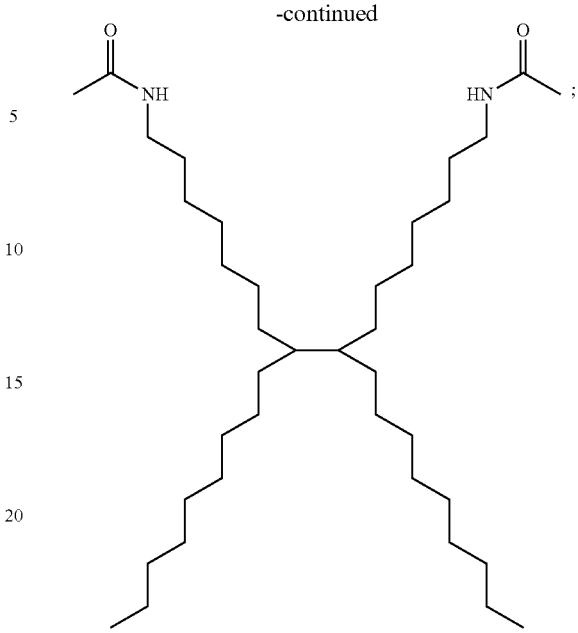

;

the method comprising:
  performing a condensation reaction between an organic carboxylic acid, which is optionally multifunctional, and an amino alcohol, which is optionally multifunctional, wherein the condensation reaction it conducted at a temperature ranging from about 150° C. to about 220° C., and optionally at reduces pressure of less than about 100 mmHg, to produce one or more compounds of General Formula II.

14. The method of claim 13, wherein the reduced pressure is less than about 100 mmHg and the condensation reaction is complete in less than about 15 hours.

15. The method of claim 13, wherein the stoichiometric ratio of the organic carboxylic acid to the amino alcohol is in the range of from about 5.0:1.0 to about 1.0:1.0, respectively.

16. The method of claim 13, wherein the compound of General Formula II that is produced is a dimer-oxazoline compound in which $R_5$ is a hydrogen.

17. The method of claim 16, further comprising:
  preparing a derivative of the dimer-oxazoline compound via a reaction with an organic isocyanate reactant or organic carboxylic acid reactant.

18. The method of claim 17, wherein preparing the derivative of the dimer-oxazoline compound is an esterification of the dimer-oxazoline compound with the organic carboxylic acid, wherein the organic carboxylic acid reactant has one or more carboxylic acid groups.

19. The method of claim 17, wherein preparing the derivative of the dimer-oxazoline compound is a condensation reaction with the organic isocyanate reactant, wherein the organic isocyanate reactant has one or more isocyanate groups, and the reaction temperature is in the range of from 0° C. to about 100° C.

20. The method of claim 19, wherein the stoichiometric ratio of the carboxylic acid or organic isocyanate reactant to the dimer-oxazoline compound is in the range of from about 0.5:1 to about 5:1.

* * * * *